(12) United States Patent
Mahableshwarkar et al.

(10) Patent No.: US 11,173,147 B2
(45) Date of Patent: Nov. 16, 2021

(54) PROPHYLACTIC OR THERAPEUTIC AGENT FOR DELIRIUM

(71) Applicant: TAKEDA PHARMACEUTICAL COMPANY LIMITED, Osaka (JP)

(72) Inventors: Atul R. Mahableshwarkar, Deerfield, IL (US); Akira Nishimura, Osaka (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 16/068,509

(22) PCT Filed: Jan. 5, 2017

(86) PCT No.: PCT/JP2017/000167
§ 371 (c)(1),
(2) Date: Jul. 6, 2018

(87) PCT Pub. No.: WO2017/119456
PCT Pub. Date: Jul. 13, 2017

(65) Prior Publication Data
US 2019/0008834 A1    Jan. 10, 2019

Related U.S. Application Data

(60) Provisional application No. 62/276,366, filed on Jan. 8, 2016.

(51) Int. Cl.
| | |
|---|---|
| A61K 31/423 | (2006.01) |
| A61P 25/20 | (2006.01) |
| A61K 31/428 | (2006.01) |
| A61P 25/00 | (2006.01) |
| A61K 31/4439 | (2006.01) |

(52) U.S. Cl.
CPC .......... A61K 31/423 (2013.01); A61K 31/428 (2013.01); A61K 31/4439 (2013.01); A61P 25/00 (2018.01); A61P 25/20 (2018.01)

(58) Field of Classification Search
CPC ......... A61K 31/423; A61P 25/00; A61P 25/20
See application file for complete search history.

(56) References Cited

U.S. PATENT DOCUMENTS

| | | | |
|---|---|---|---|
| 5,910,492 A | 6/1999 | Hoshino et al. | |
| 8,110,585 B2 | 2/2012 | Koike et al. | |
| 8,247,429 B2 | 8/2012 | Uchikawa et al. | |
| 8,273,761 B2 | 9/2012 | Uchikawa et al. | |
| 2009/0182023 A1* | 7/2009 | Uchikawa | C07D 263/52 |
| | | | 514/366 |
| 2009/0306200 A1 | 12/2009 | Hirai et al. | |
| 2010/0010038 A1 | 1/2010 | Uchikawa et al. | |
| 2010/0029707 A1 | 2/2010 | Uchikawa et al. | |
| 2010/0130538 A1 | 5/2010 | Koike et al. | |

FOREIGN PATENT DOCUMENTS

| | | |
|---|---|---|
| JP | H09-263545 A | 10/1997 |
| JP | 2009-541202 A | 11/2009 |
| WO | 1996/008466 A1 | 3/1996 |
| WO | 1997/001539 A1 | 1/1997 |
| WO | 1997/005098 A1 | 2/1997 |
| WO | 1997/032871 A1 | 9/1997 |
| WO | 2006/107027 A1 | 10/2006 |
| WO | 2007/148808 A1 | 12/2007 |
| WO | 2008/069311 A1 | 6/2008 |
| WO | 2008/084717 A1 | 7/2008 |
| WO | 2008/136382 A1 | 11/2008 |

OTHER PUBLICATIONS

Tsuda et al. (The International Journal of Psychiatry in Medicine, 2014, 47, 97-104) (Year: 2014).*
Chakraborti et al. (American Journal of Alzheimer's Disease and Other Dementias, 30, 119-129, 2015; NPL document 1 of IDS dated Dec. 3, 2018) (Year: 2015).*
Artemiou et al. (Anesthesiology and Intensive Care, 2015, 12, 126-133) (Year: 2015).*
Seglen et al. (BMJ, 1997, 314, 498-502) (Year: 1997).*
Hatta et al., "Preventive effects of ramelteon on delirium: a randomized placebo-controlled trial," JAMA Psychiatry. 71(4), 397-403. PMID: 24554232. (Year: 2014).*
Chakraborti et al., "Melatonin and Melatonin Agonist for Delirium in the Elderly Patients," American Journal of Alzheimer's Disease & Other Dementias, 2015, 30(2): 119-129.
"Delirium," Diagnostic and Statistical Manual of Psychiatric disorders, 5th Edition, 2013, p. 596-602.
Fitzgerald et al., "Delirium: A disturbance of circadian integrity?" Med. Hypotheses, 2013, 81 (4): 568-76.
Furuya et al., "Marked Improvement in Delirium with Ramelteon: Five Case Reports," Psychogeriatrics, 2012, 12: 259-262.

(Continued)

*Primary Examiner* — Theodore R. Howell
(74) *Attorney, Agent, or Firm* — Michael Best & Friedrich LLP

(57) ABSTRACT

The present invention provides a prophylactic or therapeutic agent for delirium containing compound (I) having melatonin receptor affinity. A compound represented by the formula:

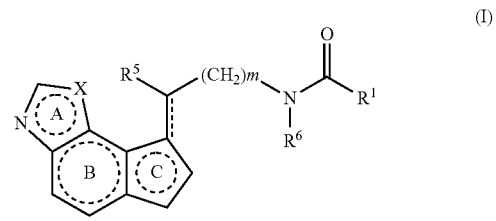

wherein each symbol is as described in the specification, or a salt thereof.

1 Claim, 5 Drawing Sheets

(56) References Cited

OTHER PUBLICATIONS

Hatta et al., "Preventive Effects of Ramelteon on Delirium, A Randomized Placebo-Controlled Trial," JAMA Psychiatry, 2014, 71(4): 397-403.
International Search Report and Written Opinion for Application No. PCT/JP2017/000167 dated Mar. 14, 2017 (8 pages).
Kimura et al., "Treatment of delirium with ramelteon: initial experience in three patients," General Hospital Psychiatry, 2011, 33: 407-409.
Ohta et al., "Melatonin Receptor Agonists for Treatment Delirium in Elderly Patients with Acute Stroke," Journal of Stroke and Cerebrovascular Diseases, 2013,22(7): 1107-1110.
Sultan et al., "Assessment of role of perioperative melatonin in prevention and treatment of postoperative delirium after hip arthroplasty under spinal anesthesia in the elderly," Saudi Journal of Anaesthesia, 2010, 4(3): 169-173.
Tsuda et al., "Ramelteon for the Treatment of Delirium Elderly Patients: A Consecutive Case Series Study," The International Journal of Psychiatry in Medicine, 2014, 47(2): 97-104.
Walker et al., "Melatonin Receptor Agonists for Delirium Prevention", Annals of Pharmacotherapy, vol. 51(1), pp. 72-78 (2017).
De Jonghe et al., "Effect of melatonin on incidence of delirium among patients with hip fracture: a multicentre, double-blind randomized controlled trial", Canadian Medical Association Journal, vol. 186(14), pp. E547-E556 (2014).
Sandberg et al., "Clinical Profile of Delirium in Older Patients," J. Am. Geriatr, Soc. 47: 1300-1306 (1999).
Misra et al., "Delirium, Depression and Anxiety," Crit. Care Clin. 19: 771-787 (2003).
Qiu et al., "Neuroprotective effects of HTR1A antagonist WAY-100635 on scopolamine-induced delirium in rats and underlying molecular mechanisms," BMC Neurosci. 17: 66 1-12 (2016).

\* cited by examiner

PROPHYLACTIC OR THERAPEUTIC AGENT FOR DELIRIUM

CROSS-REFERENCE TO RELATED APPLICATION(S)

This is a U.S. national stage entry of International Patent Application No. PCT/JP2017/000167, filed on Jan. 5, 2017, which claims priority to U.S. Provisional Patent Application No. 62/276,366, filed on Jan. 8, 2016, the entire contents of each of which are fully incorporated herein by reference.

TECHNICAL FIELD

The present invention relates to a pharmaceutical agent containing a compound possibly having melatonin receptor affinity and expected to be effective for the prophylaxis or treatment of delirium.

BACKGROUND OF THE INVENTION

Delirium is said to be among a group of neurocognitive disorders characterized by symptoms such as attention disorder (impaired ability to direct, concentrate, maintain or convert attention), disturbance of consciousness (decrease in orientation to the environment), cognitive impairment (e.g., lack of memory, disorientation, language, spatial cognition, perception) and the like. It is also said that these symptoms appear in a short period of time, show changes from the original attention and consciousness level, and has severity tending to fluctuate in the course of one day. Onset of delirium in hospitalized patients is not rare, and it is found in 14 to 24% of patients and the probability of developing delirium during hospitalization is said to be 6 to 56% of general hospitalized patients. It is said that delirium occurs in 15 to 53% of aged patients after surgery and 70 to 87% of aged patients in intensive care units. In addition, it is said that delirium occurs in 60% or more of patients in nursing homes or under post-acute care and in 83% or more of patients in the end of life stage. Furthermore, the mortality rate of delirium patients during hospitalization is high and it is said that as many as 40% of the delirium patients die in one year after diagnosis (non-patent document 1).

Therefore, families and medical sites providing care often suffer from the symptoms of delirium, and the development of a pharmaceutical agent for the prophylaxis or treatment of delirium has been desired.

As a background of the occurrence of delirium, it is suggested that the environment in which a hospitalized patient is placed disturbs the circadian rhythm of the patient, thus inducing delirium. There are reports teaching that administration of melatonin for regulating the circadian rhythm and light therapy suppresses the occurrence of delirium, and it is considered that a treatment for adjusting circadian rhythm or raising the level of endogenous melatonin may be effective for suppressing delirium (non-patent document 2).

In non-patent document 3, ramelteon was clinically administered to aged people, the prophylactic effect on delirium was verified, and the prophylactic effect of ramelteon on delirium is suggested.

In non-patent document 4, ramelteon was administered to five patients diagnosed as having delirium, the case of these five patients having recovered from delirium symptoms the next day is reported, and the use of ramelteon for delirium therapy is suggested.

In non-patent document 5, papers etc. in the past relating to ramelteon or prophylaxis or treatment of delirium with ramelteon was investigated. It reports that certain effects were suggested for the prophylaxis or treatment of delirium in aged people in two ramelteon tests, and prophylaxis of delirium in aged people was suggested in one ramelteon test.

Non-patent document 6 reports therapeutic effect of ramelteon on delirium when administered to seven patients over 65 years of age and hospitalized for acute heart failure and insomnia, and suggests that melatonin receptor agonist is effective for the treatment of delirium in aged people suffering from acute heart failure.

Non-patent document 7 reports that delirium was improved in 6 patients when ramelteon was administered to 10 patients over 65 years of age who developed delirium with heart failure etc., and suggests that ramelteon becomes a safe and useful choice that replaces melatonin in the treatment of delirium in aged people.

In non-patent document 8, ramelteon was administered to three patients who developed delirium, the therapeutic effect on delirium was examined and the possibility that ramelteon may be useful for the treatment of delirium is suggested.

In non-patent document 9, melatonin was administered to patients before and after hip joint replacement surgery under spinal anesthesia, and the document suggests that melatonin has a prophylactic or therapeutic effect on delirium.

Patent document 1 discloses use of (S)—N-[2-(1,6,7,8-tetrahydro-2H-indeno[5,4-b]furan-8-yl)ethyl]propionamide (ramelteon) as a prophylactic or therapeutic agent for night behavioral disorder associated with dementia.

Patent document 2 discloses (S)—N-[2-(2-methyl-7,8-dihydro-6H-indeno[5,4-d][1,3]oxazol-8-yl)ethyl]acetamide.

DOCUMENT LIST

Patent Documents patent document 1: WO 2006/107027
patent document 2: WO 2007/148808

Non-Patent Documents non-patent document 1: Diagnostic and Statistical Manual of Psychiatric disorders, 5th Edition [DSM-5], p. 50-59
non-patent document 2: Fitzgerald, J. M., et. al., Med. Hypotheses, 81 (4) (2013), p. 568-76
non-patent document 3: Kotaro Hatta, et. al., JAMA Psychiatry. 2014; 71(4):397-403
non-patent document 4: Motohide Furuya, et. al., Psychogeriatrics. 2012; 12:259-262
non-patent document 5: Dwaipayan Chakraborti, et. al., American Journal of Alzheimer's Disease & Other Dementias. 2015; 30 (2):119-129
non-patent document 6: Tsuyoshi Ohta, et. al., Journal of Stroke and Cerebrovascular Disease. 2013; 22(7):1107-1110
non-patent document 7: Akihiro Tsuda, et. al., Int'l. J. Psychiatry In. Medicine. 2014; 47(2):97-104
non-patent document 8: Ryo Kimura, et. al., General Hospital Psychiatry. 2011; 33:407-409
non-patent document 9: Sherif S. Sultan, et. al., Saudi Journal of Anaesthesia. 2010; 4(3):169-173

SUMMARY OF THE INVENTION

Problems to be Solved by the Invention

An object of the present invention is to provide a pharmaceutical agent comprising a compound possibly having melatonin receptor affinity and expected to be effective for the prophylaxis or treatment of delirium.

Means of Solving the Problems

The present inventors have conducted intensive studies and found that the below-mentioned compound of the present invention may be effective for the prophylaxis or treatment of delirium, which resulted in the completion of the present invention.

That is, the present invention relates to

[1] a prophylactic or therapeutic agent for delirium comprising a compound selected from
N-[2-(2-methyl-6,7-dihydro-8H-indeno[5,4-d][1,3]oxazol-8-ylidene)ethyl]acetamide,
N-[2-(2-methyl-6H-indeno[5,4-d][1,3]oxazol-8-yl)ethyl]acetamide,
N-[2-(2-methyl-6,7-dihydro-8H-indeno[5,4-d][1,3]oxazol-8-ylidene)ethyl]propionamide,
N-{2-[2-(4-phenylbutyl)-6,7-dihydro-8H-indeno[5,4-d][1,3]oxazol-8-ylidene]ethyl}acetamide,
N-[2-(2-methyl-6,7-dihydro-8H-indeno[5,4-d][1,3]thiazol-8-ylidene)ethyl]acetamide,
N-[2-(2-methyl-7,8-dihydro-6H-indeno[5,4-d][1,3]oxazol-8-yl)ethyl]acetamide,
(R)—N-[2-(2-methyl-7,8-dihydro-6H-indeno[5,4-d][1,3]oxazol-8-yl)ethyl]acetamide,
(S)—N-[2-(2-methyl-7,8-dihydro-6H-indeno[5,4-d][1,3]oxazol-8-yl)ethyl]acetamide,
N-[2-(2-methyl-7,8-dihydro-6H-indeno[5,4-d][1,3]oxazol-8-yl)ethyl]propionamide,
(R)—N-[2-(2-methyl-7,8-dihydro-6H-indeno[5,4-d][1,3]oxazol-8-yl)ethyl]propionamide,
(S)—N-[2-(2-methyl-7,8-dihydro-6H-indeno[5,4-d][1,3]oxazol-8-yl)ethyl]propionamide,
N-[2-(2-methyl-7,8-dihydro-6H-indeno[5,4-d][1,3]thiazol-8-yl)ethyl]acetamide,
(R)—N-[2-(2-methyl-7,8-dihydro-6H-indeno[5,4-d][1,3]thiazol-8-yl)ethyl]acetamide,
(S)—N-[2-(2-methyl-7,8-dihydro-6H-indeno[5,4-d][1,3]thiazol-8-yl)ethyl]acetamide,
N-[2-(2-ethyl-7,8-dihydro-6H-indeno[5,4-d][1,3]oxazol-8-yl)ethyl]acetamide,
(R)—N-[2-(2-ethyl-7,8-dihydro-6H-indeno[5,4-d][1,3]oxazol-8-yl)ethyl]acetamide,
(S)—N-[2-(2-ethyl-7,8-dihydro-6H-indeno[5,4-d][1,3]oxazol-8-yl)ethyl]acetamide,
N-[2-(2-methoxy-7,8-dihydro-6H-indeno[5,4-d][1,3]oxazol-8-yl)ethyl]acetamide,
(R)—N-[2-(2-methoxy-7,8-dihydro-6H-indeno[5,4-d][1,3]oxazol-8-yl)ethyl]acetamide, and
(S)—N-[2-(2-methoxy-7,8-dihydro-6H-indeno[5,4-d][1,3]oxazol-8-yl)ethyl]acetamide
or a salt thereof (sometimes to be abbreviated as "the compound of the present invention" in the present specification) as an active ingredient (sometimes to be abbreviated as "the agent of the present invention" in the present specification);

[2] a prophylactic or therapeutic agent for delirium comprising (S)—N-[2-(2-methyl-7,8-dihydro-6H-indeno[5,4-d][1,3]oxazol-8-yl)ethyl]acetamide or a salt thereof as an active ingredient;

[3] a method for preventing or treating delirium comprising administering an effective amount of a compound selected from
(N-[2-(2-methyl-6,7-dihydro-8H-indeno[5,4-d][1,3]oxazol-8-ylidene)ethyl]acetamide,
N-[2-(2-methyl-6H-indeno[5,4-d][1,3]oxazol-8-yl)ethyl]acetamide,
N-[2-(2-methyl-6,7-dihydro-8H-indeno[5,4-d][1,3]oxazol-8-ylidene)ethyl]propionamide,
N-{2-[2-(4-phenylbutyl)-6,7-dihydro-8H-indeno[5,4-d][1,3]oxazol-8-ylidene]ethyl}acetamide,
N-[2-(2-methyl-6,7-dihydro-8H-indeno[5,4-d][1,3]thiazol-8-ylidene)ethyl]acetamide,
N-[2-(2-methyl-7,8-dihydro-6H-indeno[5,4-d][1,3]oxazol-8-yl)ethyl]acetamide,
(R)—N-[2-(2-methyl-7,8-dihydro-6H-indeno[5,4-d][1,3]oxazol-8-yl)ethyl]acetamide,
(S)—N-[2-(2-methyl-7,8-dihydro-6H-indeno[5,4-d][1,3]oxazol-8-yl)ethyl]acetamide,
N-[2-(2-methyl-7,8-dihydro-6H-indeno[5,4-d][1,3]oxazol-8-yl)ethyl]propionamide,
(R)—N-[2-(2-methyl-7,8-dihydro-6H-indeno[5,4-d][1,3]oxazol-8-yl)ethyl]propionamide,
(S)—N-[2-(2-methyl-7,8-dihydro-6H-indeno[5,4-d][1,3]oxazol-8-yl)ethyl]propionamide,
N-[2-(2-methyl-7,8-dihydro-6H-indeno[5,4-d][1,3]thiazol-8-yl)ethyl]acetamide,
(R)—N-[2-(2-methyl-7,8-dihydro-6H-indeno[5,4-d][1,3]thiazol-8-yl)ethyl]acetamide,
(S)—N-[2-(2-methyl-7,8-dihydro-6H-indeno[5,4-d][1,3]thiazol-8-yl)ethyl]acetamide,
N-[2-(2-ethyl-7,8-dihydro-6H-indeno[5,4-d][1,3]oxazol-8-yl)ethyl]acetamide,
(R)—N-[2-(2-ethyl-7,8-dihydro-6H-indeno[5,4-d][1,3]oxazol-8-yl)ethyl]acetamide,
(S)—N-[2-(2-ethyl-7,8-dihydro-6H-indeno[5,4-d][1,3]oxazol-8-yl)ethyl]acetamide,
N-[2-(2-methoxy-7,8-dihydro-6H-indeno[5,4-d][1,3]oxazol-8-yl)ethyl]acetamide,
(R)—N-[2-(2-methoxy-7,8-dihydro-6H-indeno[5,4-d][1,3]oxazol-8-yl)ethyl]acetamide, and
(S)—N-[2-(2-methoxy-7,8-dihydro-6H-indeno[5,4-d][1,3]oxazol-8-yl)ethyl]acetamide
or a salt thereof to a mammal;

[4] a method for preventing or treating delirium comprising administering an effective amount of (S)—N-[2-(2-methyl-7,8-dihydro-6H-indeno[5,4-d][1,3]oxazol-8-yl)ethyl]acetamide or a salt thereof to a mammal;

[5] use of a compound selected from
N-[2-(2-methyl-6,7-dihydro-8H-indeno[5,4-d][1,3]oxazol-8-ylidene)ethyl]acetamide,
N-[2-(2-methyl-6H-indeno[5,4-d][1,3]oxazol-8-yl)ethyl]acetamide,
N-[2-(2-methyl-6,7-dihydro-8H-indeno[5,4-d][1,3]oxazol-8-ylidene)ethyl]propionamide,
N-{2-[2-(4-phenylbutyl)-6,7-dihydro-8H-indeno[5,4-d][1,3]oxazol-8-ylidene]ethyl}acetamide,
N-[2-(2-methyl-6,7-dihydro-8H-indeno[5,4-d][1,3]thiazol-8-ylidene)ethyl]acetamide,
N-[2-(2-methyl-7,8-dihydro-6H-indeno[5,4-d][1,3]oxazol-8-yl)ethyl]acetamide,
(R)—N-[2-(2-methyl-7,8-dihydro-6H-indeno[5,4-d][1,3]oxazol-8-yl)ethyl]acetamide,
(S)—N-[2-(2-methyl-7,8-dihydro-6H-indeno[5,4-d][1,3]oxazol-8-yl)ethyl]acetamide,
N-[2-(2-methyl-7,8-dihydro-6H-indeno[5,4-d][1,3]oxazol-8-yl)ethyl]propionamide,
(R)—N-[2-(2-methyl-7,8-dihydro-6H-indeno[5,4-d][1,3]oxazol-8-yl)ethyl]propionamide,
(S)—N-[2-(2-methyl-7,8-dihydro-6H-indeno[5,4-d][1,3]oxazol-8-yl)ethyl]propionamide, N-[2-(2-methyl-7,8-dihydro-6H-indeno[5,4-d][1,3]thiazol-8-yl)ethyl]acetamide,
(R)—N-[2-(2-methyl-7,8-dihydro-6H-indeno[5,4-d][1,3]thiazol-8-yl)ethyl]acetamide,
(S)—N-[2-(2-methyl-7,8-dihydro-6H-indeno[5,4-d][1,3]thiazol-8-yl)ethyl]acetamide,
N-[2-(2-ethyl-7,8-dihydro-6H-indeno[5,4-d][1,3]oxazol-8-yl)ethyl]acetamide,
(R)—N-[2-(2-ethyl-7,8-dihydro-6H-indeno[5,4-d][1,3]oxazol-8-yl)ethyl]acetamide,
(S)—N-[2-(2-ethyl-7,8-dihydro-6H-indeno[5,4-d][1,3]oxazol-8-yl)ethyl]acetamide,
N-[2-(2-methoxy-7,8-dihydro-6H-indeno[5,4-d][1,3]oxazol-8-yl)ethyl]acetamide,
(R)—N-[2-(2-methoxy-7,8-dihydro-6H-indeno[5,4-d][1,3]oxazol-8-yl)ethyl]acetamide, and
(S)—N-[2-(2-methoxy-7,8-dihydro-6H-indeno[5,4-d][1,3]oxazol-8-yl)ethyl]acetamide
or a salt thereof as a prophylactic or therapeutic agent for delirium;

[6] use of (S)—N-[2-(2-methyl-7,8-dihydro-6H-indeno[5,4-d][1,3]oxazol-8-yl)ethyl]acetamide or a salt thereof for the prophylaxis or treatment of delirium;

[7] use of a compound selected from
(N-[2-(2-methyl-6,7-dihydro-8H-indeno[5,4-d][1,3]oxazol-8-ylidene)ethyl]acetamide,
N-[2-(2-methyl-6H-indeno[5,4-d][1,3]oxazol-8-yl)ethyl]acetamide,
N-[2-(2-methyl-6,7-dihydro-8H-indeno[5,4-d][1,3]oxazol-8-ylidene)ethyl]propionamide,
N-{2-[2-(4-phenylbutyl)-6,7-dihydro-8H-indeno[5,4-d][1,3]oxazol-8-ylidene]ethyl}acetamide,
N-[2-(2-methyl-6,7-dihydro-8H-indeno[5,4-d][1,3]thiazol-8-ylidene)ethyl]acetamide,
N-[2-(2-methyl-7,8-dihydro-6H-indeno[5,4-d][1,3]oxazol-8-yl)ethyl]acetamide,
(R)—N-[2-(2-methyl-7,8-dihydro-6H-indeno[5,4-d][1,3]oxazol-8-yl)ethyl]acetamide,
(S)—N-[2-(2-methyl-7,8-dihydro-6H-indeno[5,4-d][1,3]oxazol-8-yl)ethyl]acetamide,
N-[2-(2-methyl-7,8-dihydro-6H-indeno[5,4-d][1,3]oxazol-8-yl)ethyl]propionamide,
(R)—N-[2-(2-methyl-7,8-dihydro-6H-indeno[5,4-d][1,3]oxazol-8-yl)ethyl]propionamide,
(S)—N-[2-(2-methyl-7,8-dihydro-6H-indeno[5,4-d][1,3]oxazol-8-yl)ethyl]propionamide,
N-[2-(2-methyl-7,8-dihydro-6H-indeno[5,4-d][1,3]thiazol-8-yl)ethyl]acetamide,
(R)—N-[2-(2-methyl-7,8-dihydro-6H-indeno[5,4-d][1,3]thiazol-8-yl)ethyl]acetamide,
(S)—N-[2-(2-methyl-7,8-dihydro-6H-indeno[5,4-d][1,3]thiazol-8-yl)ethyl]acetamide,
N-[2-(2-ethyl-7,8-dihydro-6H-indeno[5,4-d][1,3]oxazol-8-yl)ethyl]acetamide,
(R)—N-[2-(2-ethyl-7,8-dihydro-6H-indeno[5,4-d][1,3]oxazol-8-yl)ethyl]acetamide,
(S)—N-[2-(2-ethyl-7,8-dihydro-6H-indeno[5,4-d][1,3]oxazol-8-yl)ethyl]acetamide,
N-[2-(2-methoxy-7,8-dihydro-6H-indeno[5,4-d][1,3]oxazol-8-yl)ethyl]acetamide,
(R)—N-[2-(2-methoxy-7,8-dihydro-6H-indeno[5,4-d][1,3]oxazol-8-yl)ethyl]acetamide, and
(S)—N-[2-(2-methoxy-7,8-dihydro-6H-indeno[5,4-d][1,3]oxazol-8-yl)ethyl]acetamide
or a salt thereof in the production of a prophylactic or therapeutic drug for delirium;

[8] use of (S)—N-[2-(2-methyl-7,8-dihydro-6H-indeno[5,4-d][1,3]oxazol-8-yl)ethyl]acetamide or a salt thereof in the production of a prophylactic or therapeutic drug for delirium; and the like.

Effect of the Invention

According to the present invention, a pharmaceutical agent containing a compound possibly having melatonin receptor affinity as an active ingredient and expected to be effective for the prophylaxis or treatment of delirium can be provided.

DETAILED DESCRIPTION OF THE INVENTION

Figure 1:
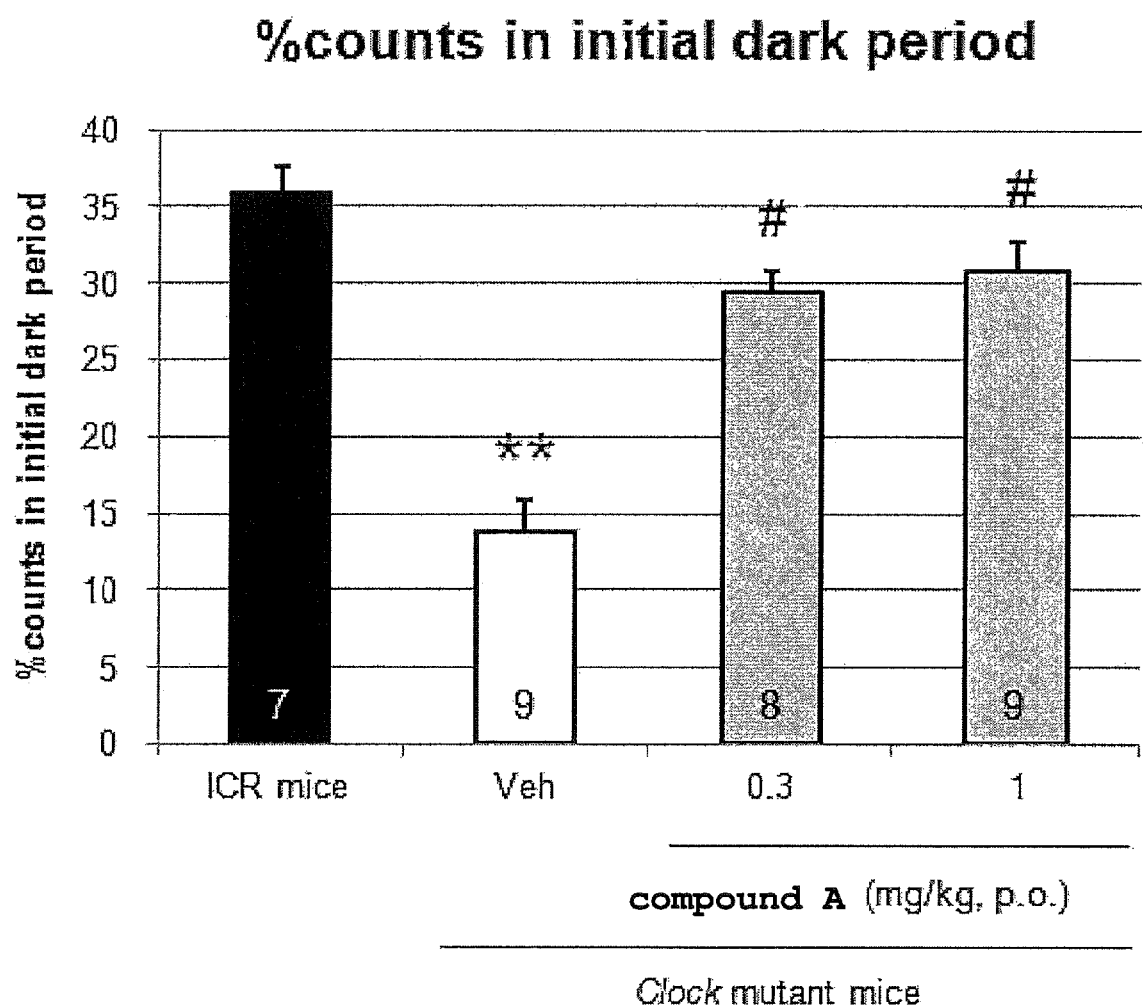
FIG. 1 shows the effect of compound A on Rotating Cage Motion of Clock mutant mice (Example 1).

Of the compounds of the present invention, (S)—N-[2-(2-methyl-7,8-dihydro-6H-indeno[5,4-d][1,3]oxazol-8-yl)ethyl]acetamide is preferable.

As the salt of the compound of the present invention, a pharmacologically acceptable salt and the like are used. Examples thereof include salts with inorganic bases, salts with organic bases, salts with inorganic acids, salts with organic acids, salts with basic or acidic amino acids and the like. Preferable examples of the salts with inorganic bases include alkali metal salts such as sodium salt, potassium salt and the like, alkaline earth metal salts such as calcium salt, magnesium salt and the like, aluminum salt, ammonium salt and the like. Preferable examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salts with inorganic acids include salts with hydrochloric acid, hydrobromic acid, nitric acid, sulfuric acid, phosphoric acid and the like. Preferable examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salts with basic amino acids include salts with arginine, lysine, ornithine and the like and preferable examples of the salts with acidic amino acids include salts with aspartic acid, glutamic acid and the like.

Particularly, a pharmaceutically acceptable salt is preferable. Examples thereof when the compound of the present invention has a basic functional group include salts with inorganic acids such as hydrochloric acid, hydrobromic acid, nitric acid, sulfuric acid, phosphoric acid and the like, and salts with organic acids such as acetic acid, phthalic acid, fumaric acid, tartaric acid, maleic acid, citric acid, succinic acid, methanesulfonic acid, p-toluenesulfonic acid and the like. Examples thereof when the compound of the present invention has an acidic functional group include alkali metal salts such as sodium salt, potassium salt and the like, alkaline earth metal salts such as calcium salt, magnesium salt and the like, ammonium salt and the like.

The compound of the present invention may be a hydrate or a non-hydrate.

The compound of the present invention can be produced according to a method known per se, for example, the production method described in WO 2007/148808 filed on Jun. 18, 2007 as a PCT application and published or a method analogous thereto.

The compound of the present invention may be a crystal, and both a single crystal and crystal mixtures are encompassed in the compound of the present invention. The crystal can be produced by crystallization by applying a crystallization method known per se.

The compound of the present invention or a salt thereof may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

The compound of the present invention encompasses solvates (e.g., hydrate) and non-solvates within the scope thereof. The compound of the present invention may be a compound labeled or substituted with an isotope (e.g., $^2$H, $^3$H, $^{11}$C, $^{14}$C, $^{18}$F, $^{35}$S, $^{125}$I). A compound labeled with or substituted by an isotope may be used, for example, as a tracer used for Positron Emission Tomography (PET) (PET tracer), and may be useful in the field of medical diagnosis and the like.

When the compound of the present invention has an asymmetric center, isomers such as enantiomer, diastereomer and the like may be present. Such isomers and a mixture thereof are all encompassed within the scope of the present invention. When an isomer is formed due to the conformation or tautomerism, such isomers and a mixture thereof are also encompassed in the compound of the present invention.

In the compound of the present invention, stereoisomers may be generated depending on the kind of the substituent. Such isomers singly or a mixture thereof are also encompassed in the present invention.

The compound of the present invention may be used as a prodrug. The prodrug of the compound of the present invention means a compound which can be converted into the compound of the present invention by reaction with an enzyme, gastric acid, or the like under physiological conditions in the living body. In other words, it means a compound which can be converted into the compound of the present invention by enzymatic oxidation, reduction, hydrolysis or the like, or a compound which can be converted into the compound of the present invention by hydrolysis with gastric acid or the like.

The compound of the present invention may be used as a prophylactic or therapeutic agent for central nervous system diseases in mammals (e.g., mouse, rat, hamster, rabbit, cat, dog, bovine, sheep, monkey, human and the like).

It may be useful as an agent for the prophylaxis or treatment of diseases, for example, (1) delirium [e.g., delirium with attention disorder, delirium with consciousness disturbance, delirium with cognitive impairment (e.g., memory deficit, disorientation, language, spatial perception, perception and the like), substance intoxication delirium (e.g., alcohol, cannabis, phencyclidine, hallucinogenic drug, inhalant, opioid, analgesic drug, sleep inducing drug, antianxiety drug, amphetamine, psychostimulant drug, cocaine, dexamethasone and the like), substance withdrawal delirium (e.g., alcohol, cannabis, phencyclidine, hallucinogenic drug, inhalant, opioid, analgesic drug, sleep inducing drug, antianxiety drug, amphetamine, psychostimulant drug, cocaine and the like), medication induced delirium (e.g., alcohol, cannabis, phencyclidine, hallucinogenic drug, inhalant, opioid, analgesic drug, sleep inducing drug, antianxiety drug, amphetamine, psychostimulant drug, cocaine and the like), delirium due to medical disease (e.g., hepatic encephalopathy and the like), acute delirium, persistent delirium, hyperactive delirium, hypoactive delirium, activity level mixed type delirium, weak delirium syndrome, delirium unaccompanied by cognitive impairment, subacute infective psychosis, subacute organic reaction, subacute psycho-organic syndrome, subacute brain syndrome, acute infective psychosis, acute organic reaction, acute psycho-organic syndrome, acute confusion state, acute brain syndrome, non-alcoholic acute confusion state, nocturnal delirium, senile nocturnal delirium, postoperative delirium, postoperative cognitive dysfunction, unspecifiable delirium (e.g., unspecifiable delirium caused by sleepless and the like], (2) psychiatric diseases [e.g., depression, major depression (with cognitive dysfunction, with anxious distress, with mixed features, with rapid cycling, with melancholic features, with atypical features, with mood congruent psychotic features, with mood incongruent psychotic features, with catatonia, with peripartum onset, with seasonal pattern etc.), bipolar disorder (e.g., bipolar 1 type disorder (e.g., manic episode, hypomanic episode, depressive episode, with anxious distress, with mixed features, with rapid cycling, with melancholic features, with mood congruent psychotic features, with mood incongruent psychotic features, with catatonia, with peripartum onset, with seasonal pattern etc.), bipolar 2 type disorder (e.g., hypomanic episode, depressive episode, with anxious distress, with mixed features, with rapid cycling, with melancholic features, with atypical features, with mood congruent psychotic features, with mood incongruent psychotic features, with catatonia, with peripartum onset, with seasonal pattern etc.), cyclothymic disorder (e.g., with anxious distress, with mixed features etc.), substance •medication induced bipolar disorder (e.g., with onset during intoxication, with onset during withdrawal and the like) and the like), substance •medication induced depressive disorder, dysthymic disorder, affective disorder (seasonal affective disorder and the like), disruptive mood dysregulation disorder, recurrent depression, postpartum depression, stress disorder, depressive symptom, mania, manic episode, depression episode, hypomanic, seasonal melancholy, myxedematous psychiatric disorder, mad hatter syndrome, grief, condolences, recurrent depressive disorder, persistent mood disorder, mood disorder, anxiety, generalized anxiety disorder, anxiety syndrome (e.g., separation anxiety, focal phobia, social anxiety, panic disorder, panic attack, agoraphobia, generalized anxiety, substance •medication-induced anxiety and the like), phobia, social phobia, social anxiety disorder, obsessive-compulsive disorder and related group (e.g., obsessive-compulsive disorder, body dysmorphic disorder, hoarding disorder, trichotillomania, excoriation disorder and the like), phobic anxiety disorder, severe stress reaction and adjustment disorder, dissociative disorder (e.g., dissociative identity disorder, dissociative amnesia, dissociative fugue, depersonalization/derealization disorder, chronic and recurrent syndromes of mixed dissociative symptoms, identity disturbance due to prolonged and intense coercive persuasion, acute dissociative reactions to stressful events, dissociative trance, Ganser's syndrome, recovery memory syndrome, etc.), somatic symptom and related disorders (e.g., somatic symptoms disorder, illness anxiety disorder, conversion disorder, factitious disorder, pseudocyesis, etc.), somatoform disorder (e.g., somatization disorder, sex change disorder, hypochondriasis, bocy dysmorphic disorder, pain disorder and the like), post-traumatic stress syndrome, post-traumatic stress disorder, reactive attachment disorder, disinhibited social engagement disorder, acute stress disorder, adjustment-like disorder, persistent complex bereavement disorder, adjustment disorder, bipolar depression, neurosis, schizophrenia (e.g., positive symptom, negative symptom, cognitive dysfunction and the like), schizophrenia spectrum disorder (e.g., personality disorder, delusional disorder, brief psychotic disorder, schizophreniform disorder, schizoaffective disorder, substance •medication-induced psychotic disorder and the like), attenuated psychosis syndrome, sustainability delusional disorder, acute and transient psychotic disorder, induced delusional disorder, schizoaffective disorder, non-organic psychotic disturbance, Capgras syndrome, Cotard's syndrome, Amok, ataque de nervios, bilis, acute confusion, brain fatigue, dahat, falling-out, blacking-out, ghost sickness, anger syndrome, koro, latah, locura, mal de ojo, nervios, Pibroktoq, qi-gong psychotic illness, rootwork, sleeping blood, neurasthnia, shen-k'uei, shin-byung, spell, susto, social phobia, zar, chronic fatigue syndrome, anxiety neurosis, compulsive neurosis, panic disorder, epilepsy, anxiety, unpleasant mental state, emotional abnormality, cyclothymia, nervous erethism, faint, addiction, sexual dysfunctions (e.g., delayed ejaculation, impotence, female orgasmic disorder, female sexual interest/arousal disorder, genito-pelvic pain/penetration disorder, hypoactive sexual desire, premature ejaculation, substance/medication-induced sexual dysfunction, lack of sexual desire, excessive libido and the like), hyperactivity disorder, attention deficit disorder, attention deficit hyperactivity disorder (ADHD), disorder of activity and attention, hyperkinetic conduct disorder, hyperkinetic disorder (e.g., oppositional defiant disorder and the like), mixed disorder of conduct and emotions (depressive conduct disorder and the like), emotional disorder, social functional disorder, psychotic major depression, refractory major depression, treatment-resistant depression, premenstrual dysphoric disorder, elimination disorders (e.g., enuresis, encopresis and the like), gender dysphoria (e.g., gender dysphoriain children, gender dysphoria in adolescents and adult, etc.), disruptive, impulse-control, and conduct disorders (e.g., oppositional defiant disorder, intermittent explosive disorder, conduct disorder, pyromania, kleptomania, pathological gambling, shopping obsessive compulsive disorder, internet addiction, compulsive sexual behavior and the like), factitious disorder (e.g., Münchhausen syndrome and the like), malingering, personality disorder group (e.g., paranoid personality disorder, schizoid personality disorder, schizotypal personality disorder, antisocial personality disorder, borderline personality disorder, histrionic personality disorder, narcissistic personality disorder, avoidant personality disorder, dependent personality disorder, obsessive personality disorder and the like), paraphilic disorders (e.g., voyeuristic disorder, exhibitionistic disorder, frotteuristic disorder, sexual masochism disorder, sexual sadism disorder, pedophilic disorder, fetishistic disorder, transvestic disorder and the like)], (3) neurodegenerative disease [e.g., Alzheimer's disease, Alzheimer-type senile dementia, Parkinson's disease, Huntington's disease, multi-infarct dementia, frontotemporal dementia, Parkinson-type frontotemporal dementia, progressive supranuclear paralysis, Pick syndrome, Niemann-Pick syndrome, degenerative diseases of basal ganglia, Down's syndrome, vascular dementia, post-encephalitis Parkinson's disease, dementia with Lewy bodies, HIV-associated dementia, amyotrophic lateral sclerosis (ALS), motor neurogenic disease (MND), Creutzfeldt-Jakob disease or prion disease, cerebral paralysis, progressive supranuclear paralysis, multiple sclerosis, spinocerebella degeneration (e.g., dentatorubural pallidoluysian atrophy and the like), neurodegeneration associated with brain trauma, neurodegeneration associated with stroke, neurodegeneration associated with cerebral infarction, neurodegeneration associated with hypoglycemia, neurodegeneration associated with epileptic seizures, neurodegeneration associated with neurotoxicosis, neurodegeneration associated with brain tumor, multiple system atrophy, vascular dementia (e.g., multiple infarct dementia, Binswanger's disease, etc.), alcoholic dementia or other drug-related dementia, dementia associated with intracranial tumor or brain trauma, dementia associated with Huntington's disease or Parkinson's disease, behavioral and psychological symptoms of dementia (BPSD) (e.g., delirium, coprophilia, delusion, hallucination, illusion, sundown syndrome and the like)], (4) pain [e.g., neuropathic pain (e.g., painful neuropathy, diabetic neuropathy, postherpetic neuralgia, postherpetic pain, backpain, trigeminal neuralgia, carpal canal syndrome, phantom limb pain, spinal cord injury and the like), chronic pain (e.g., cancer pain and the like), inflammatory pain, fibromyalgia, bursitis, tendonitis, muscular pain, articular disease (e.g., Charcot's joint, osteoarthritis, rheumatoid arthritis, hernia of intervertebral disk and the like), chronic headache, atypical facial pain, chronic abdominal pain, numbness, paralysis, itching, hyperalgesia, migraine, cluster headache, analgesia], (5) cognitive and memory impairment associated with aging [e.g., age-related memory disorders, senile dementia], (6) sleep disorder [e.g., intrinsic sleep disorder (e.g., psychophysiological insomnia and the like), extrinsic sleep disorder, circadian rhythm disorder (e.g., time zone change syndrome (jet lag), shift work sleep disorder, irregular sleep-wake pattern, delayed sleep phase syndrome, advanced sleep phase syndrome, non-24 hr sleep-wake and the like), parasomnia (e.g., arousal disorder from non-REM sleep (e.g., sleepwalking, sleep terrors, nightmare disorder, REM sleep behavior disorder, sleep bruxism, sleep talking, rhythmic movement disorder and the like), restless legs syndrome, substance medicine-induced sleep disorder and the like), sleep disorder associated with internal or psychiatric disorder (e.g., chronic obstructive pulmonary diseases, Alzheimer's disease, Parkinson's disease, cerebrovascular dementia, schizophrenia, depression, anxiety neurosis and the like), stress insomnia, insomnia (e.g., primary insomnia and the like), insomnia neurosis, narcolepsy, cataplexy, sleep apnea syndrome (e.g., obstructive sleep apnea hypopnea, central sleep apnea (e.g., idiopathic central sleep apnea, Cheyne-Stokes respiration, central sleep apnea coexisting with opioid use and the like), sleep-related hypoventilation (e.g., idiopathic hypoventilation, congenital central alveolar hypoventilation, central alveolar hypoventilation, comorbid sleep-related hypoventilation and the like) and the like), hypersomnia (e.g., primary hypersomnia and the like), sleep paralysis, periodic limb movement disorder, nocturnal myoclonus, Kleine-Levin syndrome, menstruation-related syndrome, nonrestorative sleep, sleep drunkenness, altitude insomnia, confusional arousal, sleeping spirit, nocturnal leg cramp, sleep-related erectile dysfunction, sleep-related painful erections, REM sleep-related sinus arrest, nocturnal enuresis, nocturnal paroxysmal dystonia, sleep-related abnormal swallowing syndrome, snoring, sleep-related cluster headache, sleep-related migraine, sleep-related asthma, sleep-related cardiovascular symptom (e.g., cardiac rhythm disturbance, congestive cardiac failure, valve disease, blood pressure variation and the like), sleep-related gastroesophageal reflux, esophageal hiatus hernia, sleep-related hemolysis], (7) respiratory depression caused by anesthetics, traumatic disease, or neurodegenerative disease and the like, (8) epilepsy (e.g., Dravet syndrome and the like), traumatic brain injury, cerebral apoplexy, neurotic anorexia, eating disorder (e.g., rumination disorder, avoidant/restrictive food intake disorder, anorexia nervosa, neurotic hyperorexia, binge eating disorder, atypical anorexia nervosa, purging disorder, night eating syndrome and the like), Cushing's disease, other eating disorder, alcohol dependence, alcohol abuse, alcoholic amnesia, alcohol paranoia, alcohol preference, alcohol withdrawal, alcoholic psychosis, alcohol poisoning, alcoholic jealousy, alcoholic mania, alcohol-dependent psychiatric disorder, alcoholic psychosis, drug preference, pharmacophobia, pharmacomania, drug withdrawal, acute poisoning, drug dependence, drug abuse, dependence syndrome, withdrawal symptoms with delirium, neuroleptic malignant syndrome, psychotic disturbance, amnestic syndrome, residual and tardive psychotic disturbance, dystonia, akathisia, dyskinesia, postural tremor, hyperthermia syndrome, Parkinsonism, spinobulbar muscular atrophy, spinal muscular atrophy (SMA), primary lateral sclerosis (PLS), neuroacanthocytosis, Charcot-Marie-Tooth disease (CMT), myasthenia gravis, congenital myasthenic syndrome, optic nervemyelitis, chronic inflammatory demyelinating polyneuropathy, inclusion body myositis, Crow-Fukase syndrome, multiple system atrophy (MSA), lysosome disease, adrenoleukodystrophy, mitochondria disease, subacute sclerosing panencephalitis, progressive multifocal leukoencephalopathy, HTLV1 associated myelopathy, idiopathic basal ganglia calcification, systemic amyloidosis, Ullrich disease, Willis arterial circle occlusion, distal myopathy, Bethlem myopathy, autophagic vacuolar myopathy, Danon disease, X-linked myopathy, Schwartz-Jampel syndrome, congenital myopathy, Marinesco-Sjogren's syndrome, muscular dystrophy, dystrophic myotonic syndrome, hereditary periodic paralysis, atopic myelitis, syringomyelia, myelomeningocele, Isaacs syndrome, neuroferritinopathy, superficial siderosis, Perry syndrome, frontotemporal lobar degeneration, Bickerstaff's brainstem encephalitis, acute encephalopathy with biphasic seizures and late reduced diffusion, congenital insensitivity to pain with anhydrosis, Alexander disease, Mobius syndrome, De Morsier syndrome, Aicardi syndrome, hemimegalencephaly, focal cortical dysplasia, neuronal migration disorder, congenital cerebral hypomyelination, Sturge-Weber syndrome, Arima syndrome, Mowat-Wilson syndrome, ATRX syndrome, Rothmund-Thomson syndrome, Coffin-Siris syndrome, Prader-Willi syndrome, Young-Simpson syndrome, 1p36 deletion syndrome, chromosome 14 father disomy syndrome, Emanuel syndrome, peroxisome disease, macular dystrophy, migraine, stress headache, tension headache, muscle cramps, Meniere's disease, dysautonomia, alopecia, glaucoma, hearing loss, cardiac disease, tachycardia, congestive cardiac failure, hyperpnea, bronchial asthma, apnea, sudden infant death syndrome, inflammatory diseases, allergic disease, impotence, climacteric disorder, infertility, cancer, immunodeficiency syndrome due to HIV infection, immunodeficiency syndrome due to stress, cerebrospinal meningitis, acromegaly, incontinence, metabolic syndrome, osteoporosis, peptic ulcer, irritable bowel syndrome, inflammatory intestine disease, ulcerative colitis, Crohn's disease, stress gastrointestinal disorder, nervous vomiting, diarrhea, constipation, postoperative ileus, central nerve injury (e.g., head trauma, spinal cord injury, whiplash injury and the like), ischemic central nervous disorders (e.g., cerebral infarction, cerebral hemorrhage, brain edema and the like), hyperinsulinemia, obesity, diabetes (e.g., type 1 diabetes, type 2 diabetes and the like), diabetic complications (e.g., diabetic retinopathy, diabetic neurosis, diabetic nephropathy and the like), hypertriglyceridemia (hyperlipidemia), hypertension, circulatory disease [e.g., ischemic cardiac diseases (e.g., myocardial infarction, angina pectoris and the like), cerebral apoplexy, arteriosclerosis, arterial restenosis after PTCA and the like], disease or disorder of the lower urinary tract (e.g., dysuria, incontinence and the like), reproductive and neuroendocrine diseases, convulsion, immunomodulation, ovulation control (e.g., contraception and the like), cancer (e.g., brain tumor, hypophyseal adenoma, glioma, acoustic schwannoma, retinoblastoma, thyroid cancer, pharyngeal cancer, laryngeal cancer, cancer of the tongue, thymoma, mesothelioma, breast cancer, lung cancer, non-small cell lung cancer, small cell lung cancer, gastric cancer, esophagus cancer, duodenal cancer, colorectal cancer, colorectal cancer, rectal cancer, liver cancer, hepatoma, pancreatic cancer, pancreatic endocrine tumor, bile duct cancer, gall bladder cancer, penile cancer, renal cancer, renal pelviscancer, urinary duct cancer, renal cell carcinoma, testis tumor, prostate cancer, urinary bladder cancer, vulvar cancer, uterine cancer, cervix cancer, uterine body cancer, uterus sarcoma, cholionic disease, vaginal cancer, ovary cancer, ovary germ cell tumor, skin cancer, malignant melanoma, fungoid mycosis, basalioma, soft tissue sarcoma, malignant lymphoma, Hodgkin's disease, myelodysplastic syndrome, multiple myeloma, leukemia, acute myeloid leukemia, chronic myelocytic leukemia, acute lymphocytic leukemia, chronic lymphocytic leukemia, adult T cell leukemia, chronic bone marrow proliferative disease, pancreatic endocrine tumor, fibrous histiocytoma, leiomyosarcoma, rhabdomyosarcoma, cancer of unknown primary and the like) and the like.

The compound of the present invention may be useful as an agent for the prophylaxis or treatment of a disease, particularly delirium.

The compound of the present invention may have high affinity for melatonin receptors (MT1 receptor, MT2 receptor). The compound of the present invention may act as a melatonin agonist and may be useful as a melatonin receptor affinity composition, particularly, a melatonin receptor agonist. Therefore, superior treatment effects for the above-mentioned diseases can be expected.

The compounds having melatonin receptor affinity and described in the DESCRIPTIONs of WO 96/08466 filed on Sep. 11, 1995 and published, WO 97/01539 filed on Jun. 26, 1996 and published, WO 97/05098 filed on Jul. 25, 1996 and published, WO 97/32871 filed on Mar. 5, 1997 and published, WO 2008/069311 filed on Dec. 7, 2007 and published, WO 2008/084717 filed on Dec. 27, 2007 and published, and WO 2008/136382 filed on Apr. 25, 2008 and published may also be useful for the prophylaxis, improvement of the symptoms, suppression of progression or treatment of the diseases described above, specifically, delirium and the like.

Furthermore, a compound represented by the formula

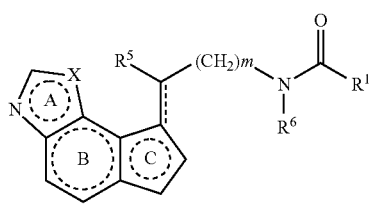
(I)

wherein $R^1$ is a hydrocarbon group optionally having substituents, amino optionally having substituents, hydroxy optionally having substituents or a heterocyclic group optionally having substituents;

$R^5$ is a hydrogen atom, a halogen atom, a hydrocarbon group optionally having substituents, amino optionally having substituents, hydroxy optionally having substituents or mercapto optionally having substituents;

$R^6$ is a hydrogen atom or a hydrocarbon group optionally having substituents;

X is an oxygen atom or a sulfur atom;

m is 0, 1 or 2;

ring A is a 5-membered ring optionally having substituents;

ring B is a 6-membered ring optionally having substituents;

ring C is a 5-membered ring optionally having substituents; and ⸗ is a single bond or a double bond, or a salt thereof (sometimes to be abbreviated as "compound (I)" in the present specification), which is described in WO 2007/148808, may also be useful for the prophylaxis or treatment of the diseases described above, specifically, delirium.

Of compounds (I), a compound represented by the formula

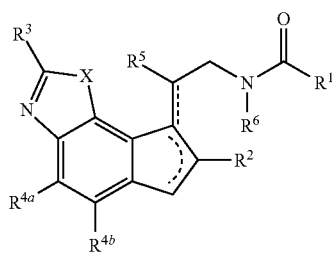
(I')

wherein $R^1$ is $C_{1-6}$ alkyl optionally having substituents, $C_{3-6}$ cycloalkyl optionally having substituents or $C_{2-6}$ alkenyl optionally having substituents;

$R^2$ is a hydrogen atom, a hydrocarbon group optionally having substituents or a heterocyclic group optionally having substituents;

$R^3$ is a hydrogen atom, $C_{1-6}$ alkyl optionally having substituents, $C_{2-6}$ alkenyl optionally having substituents or amino optionally having substituents;

$R^{4a}$ and $R^{4b}$ are the same or different and each is a hydrogen atom, a halogen atom, hydroxy optionally having substituents or $C_{1-6}$ alkyl optionally having substituents;

$R^5$ is a hydrogen atom or $C_{1-6}$ alkyl optionally having substituents; and $R^6$ is a hydrogen atom or $C_{1-6}$ alkyl optionally having substituents, or a salt thereof is preferable.

In the aforementioned formula, the ring represented by

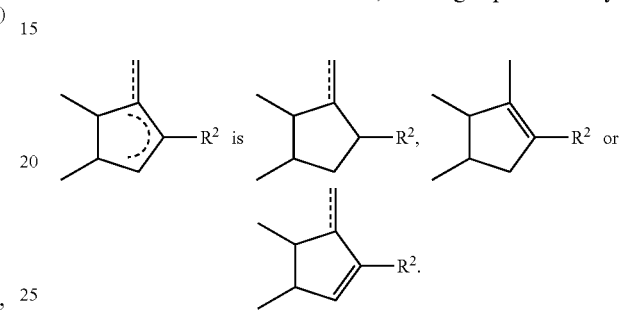

Of compounds (I), particularly a compound represented by the formula

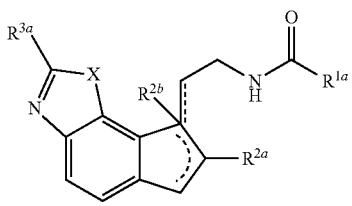

wherein $R^{1a}$ is (a) $C_{1-6}$ alkyl optionally having 1 to 3 substituents selected from $C_{1-6}$ alkyl-carbonyloxy, hydroxy and halogen atom, (b) $C_{3-6}$ cycloalkyl, (c) phenyl or (d) mono- or alkylamino;

$R^{2a}$ is a hydrogen atom or $C_{1-6}$ alkyl;

$R^{2b}$ is a hydrogen atom or hydroxy; and $R^{3a}$ is (a) a hydrogen atom, (b) $C_{1-6}$ alkyl optionally having 1 to 3 substituents selected from phenyl, hydroxy, halogen atom, $C_{1-6}$ alkyl-carbonyl, $C_{7-13}$ aralkyloxy and pyridyl, (c) $C_{3-6}$ cycloalkyl, (d) phenyl, (e) $C_{1-6}$ alkoxy, (f) mercapto, (g) $C_{1-6}$ alkylthio or (h) mono- or di-$C_{1-6}$ alkylamino, or a salt thereof is preferable.

In the aforementioned formula, the ring represented by

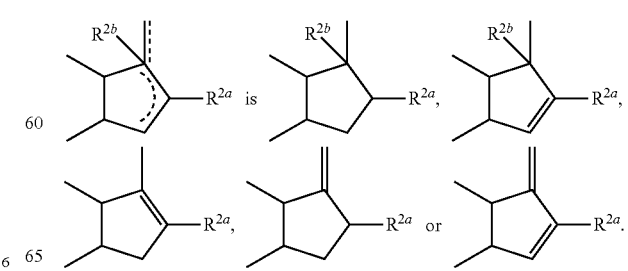

In addition, pharmaceutical agents such as tasimelteon, agomelatine, melatonin sustained release preparation, melatonin sustained release preparation for children and the like may also be useful for the prophylaxis or treatment of the diseases described above, specifically delirium and the like.

The compound of the present invention may have superior properties as a pharmaceutical product since it can be expected to be superior in solubility in water, the Japanese Pharmacopoeia dissolution test 2nd fluid or the Japanese Pharmacopoeia disintegration test 2nd fluid, can be expected to be superior in pharmacokinetics (e.g., drug half-life in blood, intracerebral transferability, metabolic stability, CYP inhibition), can be expected to have low toxicity (e.g., more superior as pharmaceutical agent in terms of acute toxicity, chronic toxicity, genetic toxicity, reproductive toxicity, cardiotoxicity, hepatotoxicity, drug interaction, carcinogenicity, phototoxicity and the like), can be expected to show few side effects and the like. Therefore, the compound of the present invention can be safely administered orally or parenterally to mammals (e.g., mouse, rat, hamster, rabbit, cat, dog, bovine, sheep, monkey, human and the like). The "parenteral" includes intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion.

The agent of the present invention may take any form of a solid dosage form such as powder, granule, tablet, capsule, orally disintegrable film or the like, or liquid such as syrup, emulsion, injection or the like.

The agent of the present invention can be produced by a conventionally-used method, for example, blending, kneading, granulation, tableting, coating, sterilization treatment, emulsification or the like according to the form thereof. As for the production of the preparation, for example, each section of the Japanese Pharmacopoeia preparation General Rules and the like can be referred to. The agent of the present invention may also be formulated as a sustained-release preparation containing the active ingredient and a biodegradable polymer compound. Such sustained-release preparation can be formulated according to the method described in JP-A-9-263545.

In the agent of the present invention, the content of the compound of the present invention varies depending on the form of the preparation. It is generally about 0.01-100 wt %, preferably about 0.1-50 wt %, further preferably about 0.5-20 wt %, as the amount of the compound of the present invention or a salt thereof relative to the whole preparation (whole pharmaceutical agent).

The compound of the present invention may be safely administered orally or parenterally as it is or as a solid agent such as powder, sweetening agent, fine granule, granule, tablet, capsule or the like or a liquid dosage form such as injection or the like by mixing with an appropriate pharmacologically acceptable carrier, for example, excipient (e.g., starch, lactose, sucrose, calcium carbonate, calcium phosphate and the like), binder (e.g., starch, gum arabic, carboxymethylcellulose, hydroxypropylcellulose, crystalline cellulose, alginic acid, gelatin, polyvinylpyrrolidone and the like), lubricant (e.g., stearic acid, magnesium stearate, calcium stearate, talc and the like), disintegrant (e.g., calcium carboxymethylcellulose, talc and the like), diluent (e.g., water for injection, saline and the like), additive (e.g., stabilizer, preservative, colorant, flavor, dissolution aid, emulsifier, buffering agent, isotonic agent and the like) as necessary and the like and processing the mixture by a conventional method. When the compound of the present invention is formulated as a preparation for topical administration, it can be directly administered to the affected parts of an articular disease and the like. In this case, it is preferable to form an injection. The compound can be administered as a parenteral agent for topical administration (e.g., intramuscular injection, subcutaneous injection, organ injection, injection into proximal part of joint and the like, a solid dosage form such as implant, granule, powder and the like, liquid such as suspension and the like, ointment etc.) or the like.

For example, When an injection is formed, the compound of the present invention is formulated into an aqueous suspension together with dispersing agent (e.g., surfactant such as Tween 80, HCO-60 and the like, polysaccharide such as carboxymethylcellulose, sodium alginate, hyaluronic acid and the like, polysorbate etc.), preservative (e.g., methylparaben, propylparaben etc.), isotonic agent (e.g., sodium chloride, mannitol, sorbitol, glucose etc.), buffering agent (e.g., calcium carbonate etc.), pH adjuster (e.g., sodium phosphate, potassium phosphate etc.) and the like, whereby a practical preparation for injection can be obtained. Alternatively, the compound is dispersed together with a vegetable oil such as sesame oil, corn oil etc., or a mixture thereof with phospholipid such as lecithin and the like or medium-chain fatty acid triglyceride (e.g., miglyol 812 etc.) to obtain an oily suspension to give an injection that can be used in practice.

The dose of the compound of the present invention varies depending on the subject of administration, administration route and symptom and is not particularly limited. For example, for oral administration to adult patients (body weight about 40-80 kg, for example, 60 kg) with delirium, the dose as the compound of the present invention is, for example, 0.001-1000 mg/kg body weight, preferably 0.01-100 mg/kg body weight, further preferably 0.1-10 mg/kg body weight, per day. This amount may be administered in one to three portions per day.

The agent of the present invention may be safely administered solely or in the form of a pharmaceutical composition, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection (e.g., bolus), intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop or the like, which are obtained by mixing with a pharmacologically acceptable carrier according to a method known per se (e.g., the method described in the Japanese Pharmacopoeia etc.) as the production method of a pharmaceutical preparation, orally or parenterally (e.g., intravenous, intramuscular, subcutaneous, intraorgan, intranasal, intradermal, instillation, intracerebral, intrarectal, intravaginal and intraperitoneal administrations, and administration to lesion).

As the aforementioned "pharmacologically acceptable carrier", various organic or inorganic carriers conventionally used as preparation materials (starting materials) may be used. For example, excipient, lubricant, binder and disintegrant and the like may be used for solid preparations, and solvent, solubilizing agent, suspending agent, isotonic agent, buffering agent, and soothing agent and the like may be used for liquid preparations. Where necessary, preparation additives such as preservative, antioxidant, colorant, sweetening agent and the like may be used.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, isotonic brine, 5% dextrose, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidant include sulfites, ascorbic acid, α-tocopherol and the like.

The pharmaceutical composition can be produced according to a conventional method by adding the compound of the present invention in a proportion of generally 0.01-100% (w/w), preferably 0.1-95% (w/w), relative to the total amount of the preparation, though subject to change depending on the dosage form, administration method, carrier and the like.

The compound of the present invention can be expected to have extremely low toxicity, can be used for the prophylaxis or treatment of delirium by combining with other pharmaceutical agent, and can be expected to show a superior prophylactic or therapeutic effect by such combined use with other pharmaceutical agents. It can also be expected to reduce side effects of other pharmaceutical agents by reducing the dose thereof by such combination therapy.

As such pharmaceutical agents that can be used in combination with the compound of the present invention (hereinafter to be abbreviated as concomitant drug), the following can be mentioned.

Benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), mirtazapine, trazodone hydrochloride, nefazodone hydrochloride, bupropion hydrochloride, setiptiline maleate, 5-HT1A agonist, (buspirone hydrochloride, tandospirone citrate, osemozotan hydrochloride etc.), 5-HT3 antagonist (cyamemazine etc.), non-cardioselective β inhibitor (propranolol hydrochloride, oxprenolol hydrochloride etc.), histamine H1 antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (Aprepitant, saredutant etc.), pharmaceutical agent acting on metabolic glutamic acid receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-HT2A antagonist, 5-HT2A inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcohol dependency, therapeutic drug for autism, therapeutic drug for chronic fatigue syndrome, therapeutic drug for convulsion, therapeutic drug for fibromyalgia, therapeutic drug for headache, therapeutic drug for insomnia (etizolam, zopiclone, triazolam, zolpidem, ramelteon, indiplon etc.), therapeutic drug for smoking cessation, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambling, therapeutic drug for restless leg syndrome of lower limb, therapeutic drug for substance dependence, therapeutic drug for alcohol related diseases, therapeutic drug for irritable bowel syndrome, therapeutic drug for Alzheimer's disease (donepezil, galanthamine etc.), therapeutic drug for Parkinson's disease, therapeutic drug for Huntington's disease, therapeutic drug for ALS (riluzole etc., neurotrophic factor etc.), therapeutic drug for dyslipemia such as cholesterol lowering drug (statin series (pravastatin sodium, atorvastatin, simvastatin, rosuvastatin etc.), fibrate (clofibrate etc.), squalene synthetase inhibitor), therapeutic drug for abnormal behavior or inhibitor of wandering habit due to dementia (sedative, antianxiety drug etc.), apoptosis inhibitor, antiobesity drug, therapeutic drug for diabetes, therapeutic drug for hypertension, therapeutic drug for hypotension, therapeutic drug for rheumatoid (DMARD), anti-cancer agent, therapeutic drug for parathyroid (PTH), calcium receptor antagonist, sex hormone or a derivative thereof (progesterone, estradiol, estradiol benzoate etc.), neuronal differentiation promoting agent, nerve regeneration promoting drug, non-steroidal antiinflammatory agent (meloxicam, tenoxicam, indomethacin, ibuprofen, celecoxib, rofecoxib, aspirin, indomethacin etc.), steroid (dexamethasone, cortisone acetate etc.), anti-cytokine drug (TNF inhibitor, MAP kinase inhibitor etc.), antibody preparation, nucleic acid or nucleic acid derivative, aptamer drug and the like.

In the following, combined use of the compound of the present invention and a concomitant drug is indicated by "the combination agent of the present invention".

Two or more kinds of the above-mentioned concomitant drugs may be used in combination at an appropriately ratio.

When the compound of the present invention is used in combination with concomitant drugs, the amounts of the drugs may be decreased within a safe range in consideration of the counter effect of the drugs. Therefore, the counter effect presumably induced by these drugs can be prevented safely.

The compound of the present invention may be used in combination with a non-drug therapy. Specific examples of the non-drug therapy include (1) surgery; (2) pressurized chemotherapy using angiotensin II and the like; (3) gene therapy; (4) hyperthermia therapy; (5) cryotherapy; (6) laser ablation method; (7) radiation therapy; (8) immunotherapy; (9) regenerative therapy; (10) cell therapy method; (11) psychotherapy or psychosocial therapy.

These concomitant drugs may be free forms or pharmaceutically acceptable salts. Examples of such salt when the drug has an acidic functional group include inorganic salts such as alkali metal salt (e.g., sodium salt, potassium salt and the like), alkaline earth metal salt (e.g., calcium salt, magnesium salt, barium salt and the like) and the like, ammonium salt and the like. Examples thereof when the drug has a basic functional group include salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like. The concomitant drugs exemplified here can be easily obtained as commercially available products or can be produced according to a known method.

The administration form of the combination agent of the present invention is not particularly limited, and the compound of the present invention and a concomitant drug may be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention; the concomitant drug, or in the reverse order) and the like.

The dose of the concomitant drug may be appropriately selected using the clinically-used dose as the standard. In addition, the mixing ratio of the compound of the present invention and the concomitant drugs may be appropriately selected according to the subject of administration, administration route, symptom, the kind of the concomitant drug used and the like. Generally, it may be determined using the general dose of the concomitant drug as the standard. When the subject of administration is human, for example, 0.01-100 parts by weight of the concomitant drug is used per part by weight of the compound of the present invention.

The combination agent in the present invention is expected to have low toxicity. For example, the compound of the present invention or(and) the above-mentioned concomitant drug are mixed with a pharmacologically acceptable carrier according to a known method and a pharmaceutical composition, for example, tablet (including sugar-coated tablet, film-coated tablet), powder, granule, capsule (including soft capsule), liquid, injection, suppository, sustained-release preparation and the like can be prepared. These compositions can be safely administered orally or parenterally (e.g., topical, rectal, intravenous administration etc.). Injection can be administered intravenously, intramuscularly, subcutaneously or by intraorgan administration or direct administration to the lesion.

The pharmacologically acceptable carrier, which may be used for the production of the combination agent of the present invention, is exemplified by various organic or inorganic carrier materials that are conventionally used as preparation materials, for example, excipient, lubricant, binding agent and disintegrant for solid preparations; or solvent, solubilizing agent, suspending agent, isotonic agent, buffering agent, soothing agent and the like for liquid preparations. Where necessary, conventional preservative, antioxidant, colorant, sweetening agent, adsorbing agent, wetting agent and the like may also be used as appropriate.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, isotonic brine, 5% dextrose, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol), polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidant include sulfites, ascorbic acid, α-tocopherol and the like.

The mixing ratio of the compound of the present invention and a concomitant drug in the combination agent of the present invention may be appropriately selected based on the subject of administration, administration route, disease and the like.

For example, while the content of the compound of the present invention in the combination agent of the present invention varies depending on the preparation form, it is generally about 0.01—about 100 wt %, preferably about 0.1—about 50 wt %, more preferably about 0.5—about 20 wt %, of the preparation.

The content of the concomitant drug in the combination agent of the present invention varies depending on the preparation form, and generally about 0.01 to about 100% by weight, preferably about 0.1 to about 50% by weight, further preferably about 0.5 to about 20% by weight, of the preparation.

While the content of the additive such as a carrier and the like in the combination agent of the present invention varies depending on the form of a preparation, it is generally about 1 to about 99.99% by weight, preferably about 10 to about 90% by weight, based on the preparation.

When the compound of the present invention and the concomitant drug are separately prepared, the contents thereof are the same as above.

EXAMPLES

While the present invention is explained in detail by further referring to the following Production Examples, Examples and Preparation Example, they are mere Production Examples, Examples and Preparation Example and do not limit the present invention.

The compounds in the following Production Examples can be produced by a method known per se, for example, Reference Examples and Examples described in WO 2007/148808 filed on Jun. 18, 2007 as a PCT application and published or a method analogous thereto.

In the following Examples and Preparation Example, (S)—N-[2-(2-methyl-7,8-dihydro-GH-indeno[5,4-d][1,3]oxazol-8-yl)ethyl]acetamide (compound of Production Example 12) is compound A.

Production Example 1

N-[2-(6,7-dihydro-8H-indeno[5,4-d][1,3]oxazol-8-ylidene)ethyl]acetamide

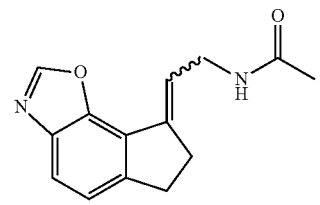 [SMILES: CC(=O)NCC=C1CCc2ccc3ncoc3c21]

Production Example 2

N-[2-(6,7-dihydro-8H-indeno[5,4-d][1,3]oxazol-8-ylidene)ethyl]propionamide

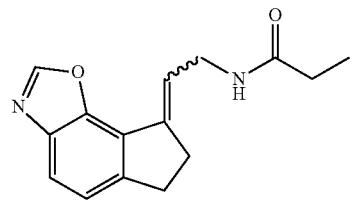 [SMILES: CCC(=O)NCC=C1CCc2ccc3ncoc3c21]

Production Example 3

N-[2-(2-methyl-6,7-dihydro-8H-indeno[5,4-d][1,3]oxazol-8-ylidene)ethyl]acetamide

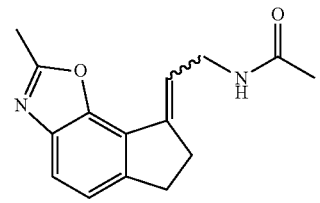 [SMILES: CC(=O)NCC=C1CCc2ccc3nc(C)oc3c21]

Production Example 4

N-[2-(2-methyl-6H-indeno[5,4-d][1,3]oxazol-8-yl)ethyl]acetamide

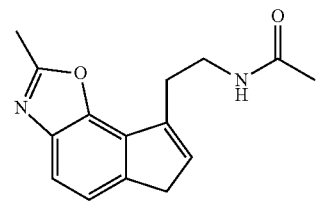 [SMILES: CC(=O)NCCC1=CCc2ccc3nc(C)oc3c21]

Production Example 5

N-[2-(2-methyl-6,7-dihydro-8H-indeno[5,4-d][1,3]oxazol-8-ylidene)ethyl]propionamide

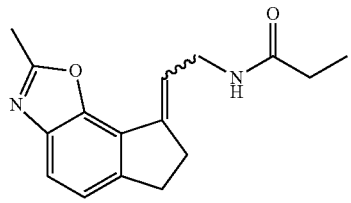 [SMILES: CCC(=O)NCC=C1CCc2ccc3nc(C)oc3c21]

Production Example 6

N-{2-[2-(4-phenylbutyl)-6,7-dihydro-8H-indeno[5,4-d][1,3]oxazol-8-ylidene]ethyl}acetamide

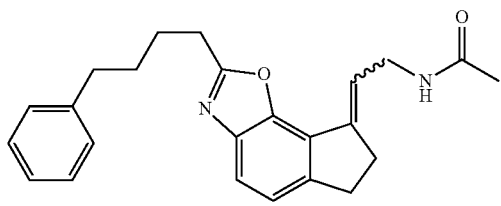 [SMILES: CC(=O)NCC=C1CCc2ccc3nc(CCCCc4ccccc4)oc3c21]

Production Example 7

N-{2-[2-(4-phenylbutyl)-6,7-dihydro-8H-indeno[5,4-d][1,3]oxazol-8-ylidene]ethyl}propionamide

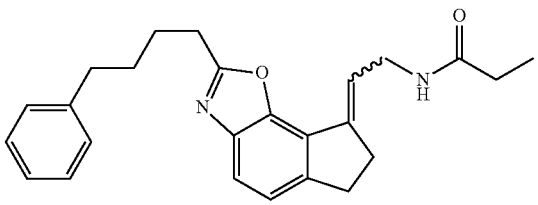 [SMILES: CCC(=O)NCC=C1CCc2ccc3nc(CCCCc4ccccc4)oc3c21]

Production Example 8

N-[2-(2-methyl-6,7-dihydro-8H-indeno[5,4-d][1,3]thiazol-8-ylidene)ethyl]acetamide

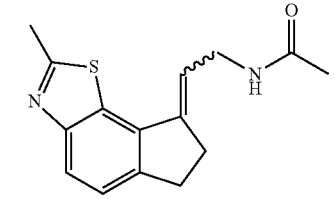 [SMILES: CC(=O)NCC=C1CCc2ccc3nc(C)sc3c21]

Production Example 9

N-[2-(7,8-dihydro-6H-indeno[5,4-d][1,3]oxazol-8-yl)ethyl]acetamide

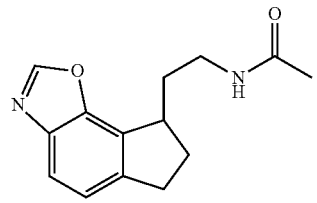 [SMILES: CC(=O)NCCC1CCc2ccc3ncoc3c21]

Production Example 10

N-[2-(7,8-dihydro-6H-indeno[5,4-d][1,3]oxazol-8-yl)ethyl]propionamide

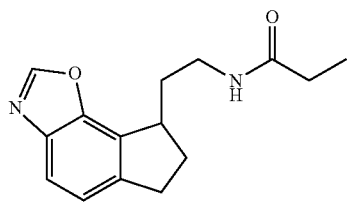 [SMILES: CCC(=O)NCCC1CCc2ccc3ncoc3c21]

Production Example 11

N-[2-(2-methyl-7,8-dihydro-6H-indeno[5,4-d][1,3]oxazol-8-yl)ethyl]acetamide

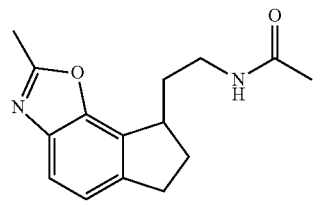

Production Example 12

(S)—N-[2-(2-methyl-7,8-dihydro-6H-indeno[5,4-d][1,3]oxazol-8-yl)ethyl]acetamide

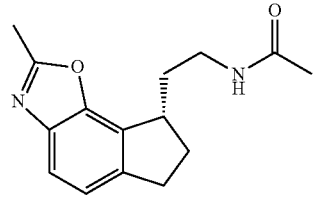 [SMILES: CC(=O)NCC[C@@H]1CCc2ccc3nc(C)oc3c21]

Production Example 13

(R)—N-[2-(2-methyl-7,8-dihydro-6H-indeno[5,4-d][1,3]oxazol-8-yl)ethyl]acetamide

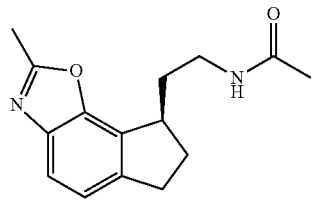 [SMILES: CC(=O)NCC[C@H]1CCc2ccc3nc(C)oc3c21]

Production Example 14

N-[2-(2-methyl-7,8-dihydro-6H-indeno[5,4-d][1,3]oxazol-8-yl)ethyl]propionamide

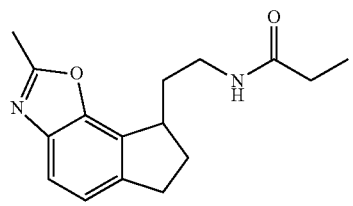 [SMILES: CCC(=O)NCCC1CCc2ccc3nc(C)oc3c21]

Production Example 15

(S)—N-[2-(2-methyl-7,8-dihydro-6H-indeno[5,4-d][1,3]oxazol-8-yl)ethyl]propionamide

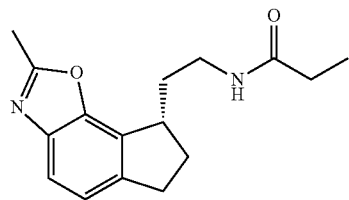 [SMILES: CCC(=O)NCC[C@@H]1CCc2ccc3nc(C)oc3c21]

Production Example 16

(R)—N-[2-(2-methyl-7,8-dihydro-6H-indeno[5,4-d][1,3]oxazol-8-yl)ethyl]propionamide

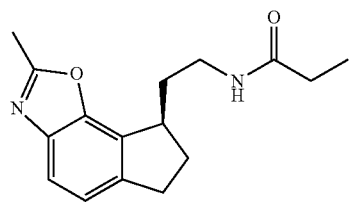 [SMILES: CCC(=O)NCC[C@H]1CCc2ccc3nc(C)oc3c21]

Production Example 17

N-{2-[2-(4-phenylbutyl)-7,8-dihydro-6H-indeno[5,4-d][1,3]oxazol-8-yl]ethyl}acetamide

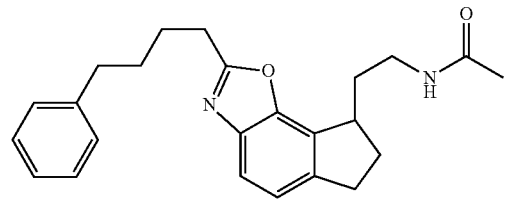 [SMILES: CC(=O)NCCC1CCc2ccc3nc(CCCCc4ccccc4)oc3c21]

Production Example 18

N-{2-[2-(4-phenylbutyl)-7,8-dihydro-6H-indeno[5,4-d][1,3]oxazol-8-yl]ethyl}propionamide

Production Example 19

N-[2-(2-methyl-7,8-dihydro-6H-indeno[5,4-d][1,3]thiazol-8-yl)ethyl]acetamide

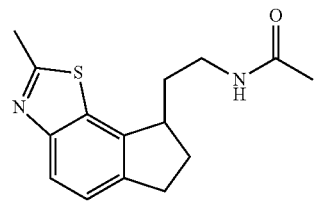

Production Example 20

(S)—N-[2-(2-methyl-7,8-dihydro-6H-indeno[5,4-d][1,3]thiazol-8-yl)ethyl]acetamide

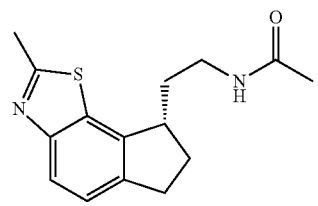 [SMILES: CC(=O)NCC[C@@H]1CCc2ccc3nc(C)sc3c21]

Production Example 21

(R)—N-[2-(2-methyl-7,8-dihydro-6H-indeno[5,4-d][1,3]thiazol-8-yl)ethyl]acetamide

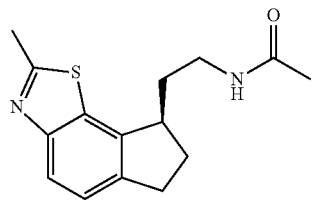 [SMILES: CC(=O)NCC[C@H]1CCc2ccc3nc(C)sc3c21]

Production Example 22

N-[2-(2-ethyl-7,8-dihydro-6H-indeno[5,4-d][1,3]oxazol-8-yl)ethyl]acetamide

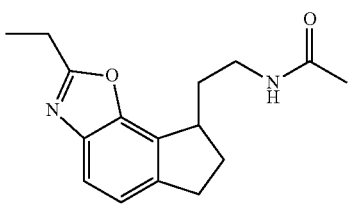 [SMILES: CCc1nc2ccc3c(c2o1)C(CCNC(C)=O)CC3]

Production Example 23

N-{2-[2-(hydroxymethyl)-7,8-dihydro-6H-indeno[5,4-d][1,3]oxazol-8-yl]ethyl}acetamide

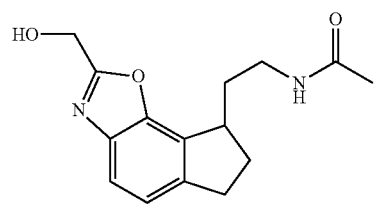 [SMILES: CC(=O)NCCC1CCc2ccc3nc(CO)oc3c21]

Production Example 24

N-[2-(2-isopropyl-7,8-dihydro-6H-indeno[5,4-d][1,3]oxazol-8-yl)ethyl]acetamide

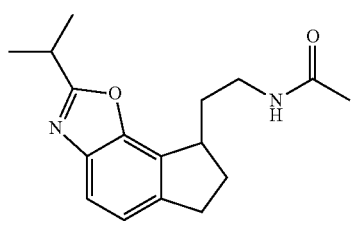 [SMILES: CC(=O)NCCC1CCc2ccc3nc(C(C)C)oc3c21]

Production Example 25

N-{2-[2-(trifluoromethyl)-7,8-dihydro-6H-indeno[5,4-d][1,3]oxazol-8-yl]ethyl}acetamide

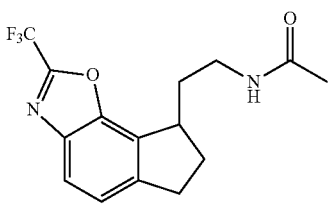 [SMILES: CC(=O)NCCC1CCc2ccc3nc(C(F)(F)F)oc3c21]

Production Example 26

N-{2-[2-(4-hydroxybutyl)-7,8-dihydro-6H-indeno[5,4-d][1,3]oxazol-8-yl]ethyl}acetamide

Production Example 27

N-{2-[2-(3-hydroxybutyl)-7,8-dihydro-6H-indeno[5,4-d][1,3]oxazol-8-yl]ethyl}acetamide

Production Example 28

N-{2-[2-(3-oxobutyl)-7,8-dihydro-6H-indeno[5,4-d][1,3]oxazol-8-yl]ethyl}acetamide

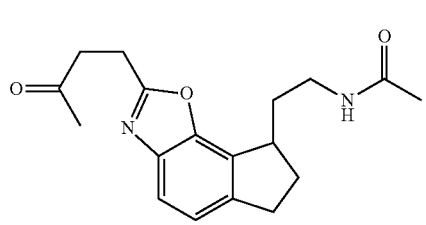 [SMILES: CC(=O)CCc1nc2ccc3c(c2o1)C(CCNC(C)=O)CC3]

29

Production Example 29

N-[2-(2-cyclopropyl-7,8-dihydro-6H-indeno[5,4-d][1,3]oxazol-8-yl)ethyl]acetamide

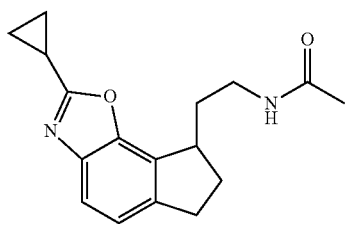 [SMILES: CC(=O)NCCC1CCc2ccc3nc(C4CC4)oc3c21]

Production Example 30

N-[2-(2-phenyl-7,8-dihydro-6H-indeno[5,4-d][1,3]oxazol-8-yl)ethyl]acetamide

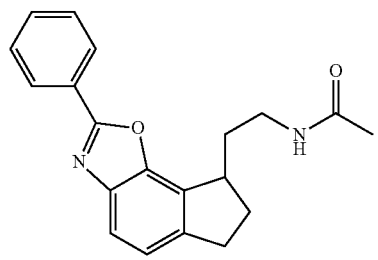 [SMILES: CC(=O)NCCC1CCc2ccc3nc(-c4ccccc4)oc3c21]

Production Example 31

N-[2-(2-benzyl-7,8-dihydro-6H-indeno[5,4-d][1,3]oxazol-8-yl)ethyl]acetamide

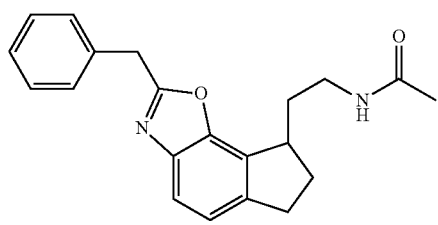 [SMILES: CC(=O)NCCC1CCc2ccc3nc(Cc4ccccc4)oc3c21]

30

Production Example 32

N-{2-[2-(2-phenylethyl)-7,8-dihydro-6H-indeno[5,4-d][1,3]oxazol-8-yl]ethyl}acetamide

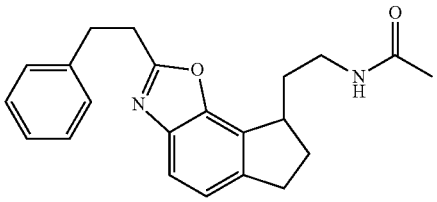 [SMILES: CC(=O)NCCC1CCc2ccc3nc(CCc4ccccc4)oc3c21]

Production Example 33

N-{2-[2-(3-phenylpropyl)-7,8-dihydro-6H-indeno[5,4-d][1,3]oxazol-8-yl]ethyl}acetamide

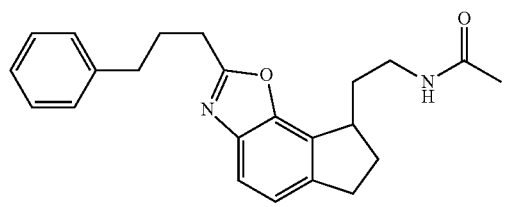 [SMILES: CC(=O)NCCC1CCc2ccc3nc(CCCc4ccccc4)oc3c21]

Production Example 34

N-(2-{2-[(benzyloxy)methyl]-7,8-dihydro-6H-indeno[5,4-d][1,3]oxazol-8-yl}ethyl)acetamide

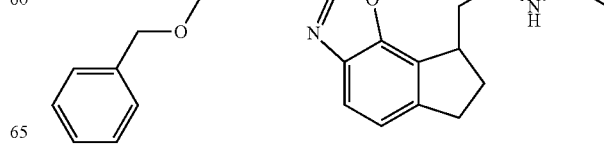

Production Example 35

N-(2-{2-[4-(benzyloxy)butyl]-7,8-dihydro-6H-indeno[5,4-d][1,3]oxazol-8-yl}ethyl)acetamide

31

Production Example 36

N-(2-{2-[3-(benzyloxy)butyl]-7,8-dihydro-6H-in-deno[5,4-d][1,3]oxazol-8-yl}ethyl)acetamide

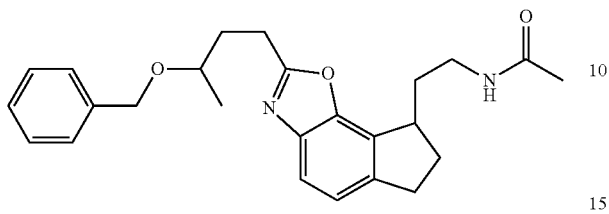

Production Example 37

N-{2-[2-(4-pyridin-2-ylbutyl)-7,8-dihydro-6H-in-deno[5,4-d][1,3]oxazol-8-yl]ethyl}acetamide

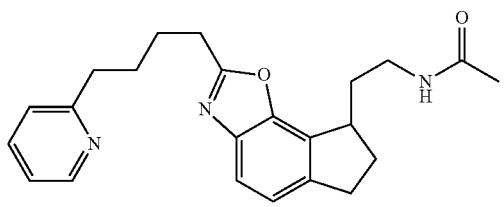

Production Example 38

N-[2-(2-methoxy-7,8-dihydro-6H-indeno[5,4-d][1,3]oxazol-8-yl)ethyl]acetamide

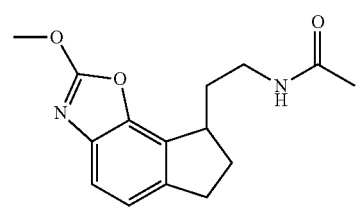 [SMILES: COc1nc2ccc3c(c2o1)C(CCNC(C)=O)CC3]

Production Example 39

N-{2-[2-(methylthio)-7,8-dihydro-6H-indeno[5,4-d][1,3]oxazol-8-yl]ethyl}acetamide

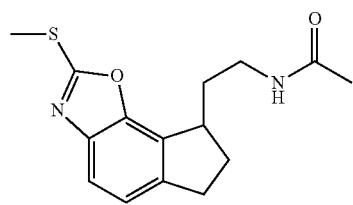

32

Production Example 40

N-{2-[2-(dimethylamino)-7,8-dihydro-6H-indeno[5,4-d][1,3]oxazol-8-yl]ethyl}acetamide

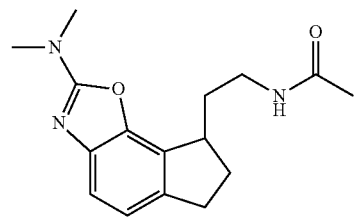 [SMILES: CC(=O)NCCC1CCc2ccc3nc(N(C)C)oc3c21]

Production Example 41

1-methyl-2-{[2-(2-methyl-7,8-dihydro-6H-indeno[5,4-d][1,3]oxazol-8-yl)ethyl]amino}-2-oxoethyl acetate

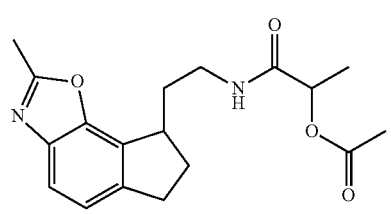 [SMILES: CC(=O)OC(C)C(=O)NCCC1CCc2ccc3nc(C)oc3c21]

Production Example 42

2-hydroxy-N-[2-(2-methyl-7,8-dihydro-6H-indeno[5,4-d][1,3]oxazol-8-yl)ethyl]propanamide

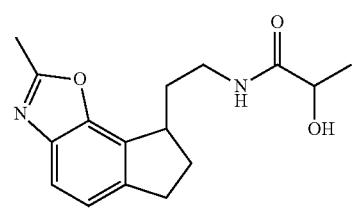 [SMILES: Cc1nc2ccc3c(c2o1)C(CCNC(=O)C(C)O)CC3]

Production Example 43

N-[2-(2-methyl-7,8-dihydro-6H-indeno[5,4-d][1,3]oxazol-8-yl)ethyl]cyclopropanecarboxamide

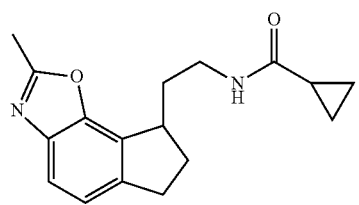 [SMILES: Cc1nc2ccc3c(c2o1)C(CCNC(=O)C1CC1)CC3]

Production Example 44

N-[2-(2-methyl-7,8-dihydro-6H-indeno[5,4-d][1,3]oxazol-8-yl)ethyl]benzamide

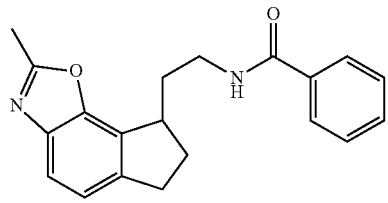 [SMILES: Cc1nc2ccc3c(c2o1)C(CCNC(=O)c1ccccc1)CC3]

Production Example 45

2,2,2-trifluoro-N-[2-(2-methyl-7,8-dihydro-6H-indeno[5,4-d][1,3]oxazol-8-yl)ethyl]acetamide

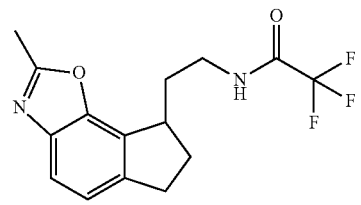 [SMILES: Cc1nc2ccc3c(c2o1)C(CCNC(=O)C(F)(F)F)CC3]

Production Example 46

1-ethyl-3-[2-(2-methyl-7,8-dihydro-6H-indeno[5,4-d][1,3]oxazol-8-yl)ethyl]urea

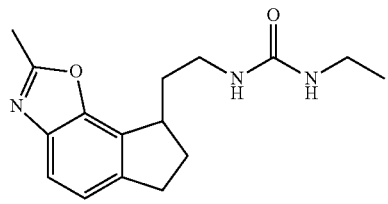 [SMILES: CCNC(=O)NCCC1CCc2ccc3nc(C)oc3c21]

Production Example 47

N-[2-(2-mercapto-7,8-dihydro-6H-indeno[5,4-d][1,3]oxazol-8-yl)ethyl]acetamide

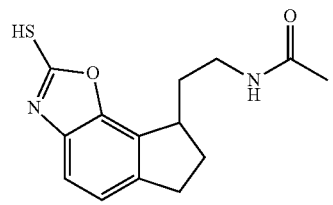 [SMILES: CC(=O)NCCC1CCc2ccc3nc(S)oc3c21]

Production Example 48

N-[2-(8-hydroxy-7-isopropyl-2-methyl-7,8-dihydro-6H-indeno[5,4-d][1,3]oxazol-8-yl)ethyl]acetamide

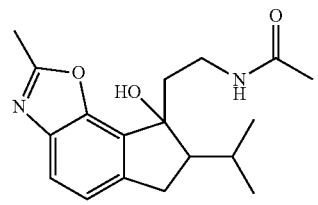 [SMILES: CC(=O)NCCC1(O)c2c(ccc3nc(C)oc23)CC1C(C)C]

Production Example 49

N-[2-(7-isopropyl-2-methyl-6H-indeno[5,4-d][1,3]oxazol-8-yl)ethyl]acetamide

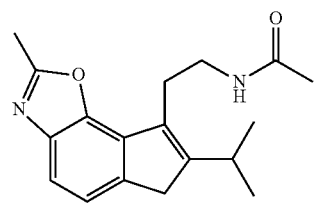 [SMILES: CC(=O)NCCC1=C(C(C)C)Cc2ccc3nc(C)oc3c21]

Example 1

Effect on Phase Delay of Compound A in Clock Mutant Mouse

1. Method 1.1 Animal

Male Clock mutant mouse (Trans Genic Inc.) and male ICR mouse (CLEA Japan Inc.) were used as a wild-type control in this study. All animals were bred in groups of 4 or 5 animals per cage in a light control room (lights on at 7:00 and 12 hour light/dark cycle) prior to behavioral test. Food and tap water were freely provided.

1.2 Measurement

21-Week-old and 23-week-old mice were used in experiment 1 and experiment 2 (in each experiment, Clock mutant mouse; n=36, ICR mouse; n=12). In both experiments, the animals were placed in a test room and individually bred under 10 hr/14 hr light/dark cycle (lights on at 7:00 and lights off at 17:00) in a cage provided with a rotating basket (diameter 14.5 cm). In addition, 15 Clock mutant mice and 10 ICR mice were prepared as extra animals in the same room in each experiment. Data on the rotating basket exercise were collected every minute and analyzed using Clocklab (registered trade mark) (Actimetrics, Evanston, Ill., USA).

The animals were first acclimated to a new light/dark cycle for about 2 weeks. In the acclimation period, a total number of exercises in 24 hours (total number) for each day, and the percentage of the number of exercise in the light period (7:00 to 17:00) (percentage in the light period) in the total number were measured. Animals that did not satisfy the following criteria, that is, average % in the light period of not more than 10 for ICR mouse and not more than 25 for Clock mutant mouse, and average total number (number/min) of not less than 10 for ICR mouse and not less than 5 for Clock mutant mouse, were removed and replaced with the extra animal.

In the preliminary treatment period, the mice were orally administered with a solvent (0.5% methylcellulose solution) at 15:45-16:19 once daily for 2 weeks for acclimation to administration prior to the drug treatment period. Then, animals that did not meet the above criteria were removed, Clock mutant mice were divided into 3 groups (n=8-9) of solvent treatment (sometimes to be abbreviated as Veh in the present specification and drawings), compound A at dose of 0.3, 1 mg/kg (experiment 1) and compound A at dose of 0.003, 0.03 mg/kg (experiment 2), such that the percentage of the number of exercise in 3 hours of the initial dark period (17:00-20:00) in the total number (% in the initial dark period), and the average total number (number/min) of the groups before drug treatment were not significantly different. The solvent or compound A was orally administered to the animals at 15:45 to 16:13 once a day for 7 days.

In the drug treatment period, % in the initial dark period was measured, and the exercise start time was measured using same as an additional index in the Clock mutant mice. Using the aforementioned parameter, the minimum effective dose of compound A in these experiments (experiments 1 and 2) was determined.

1.3 Statistics

The data are shown in average ±SEM. A statistical significance between ICR mouse and Clock mutant mouse was determined by Student's t-test (experiment 1) or Aspin-Welch test (experiment 2) in which P≤0.05 was significant. For analysis of multiple administration of compound A, the statistical significance was determined by one-sided Williams' 20 test (experiments 1 and 2) in which P≤0.025 was significant.

2. Results and Discussion

During the acclimation period in experiment 1, one Clock mutant mouse died. The death did not influence the results of this experiment because the mouse was replaced by an extra animal during the preliminary treatment period.

Figure 2:
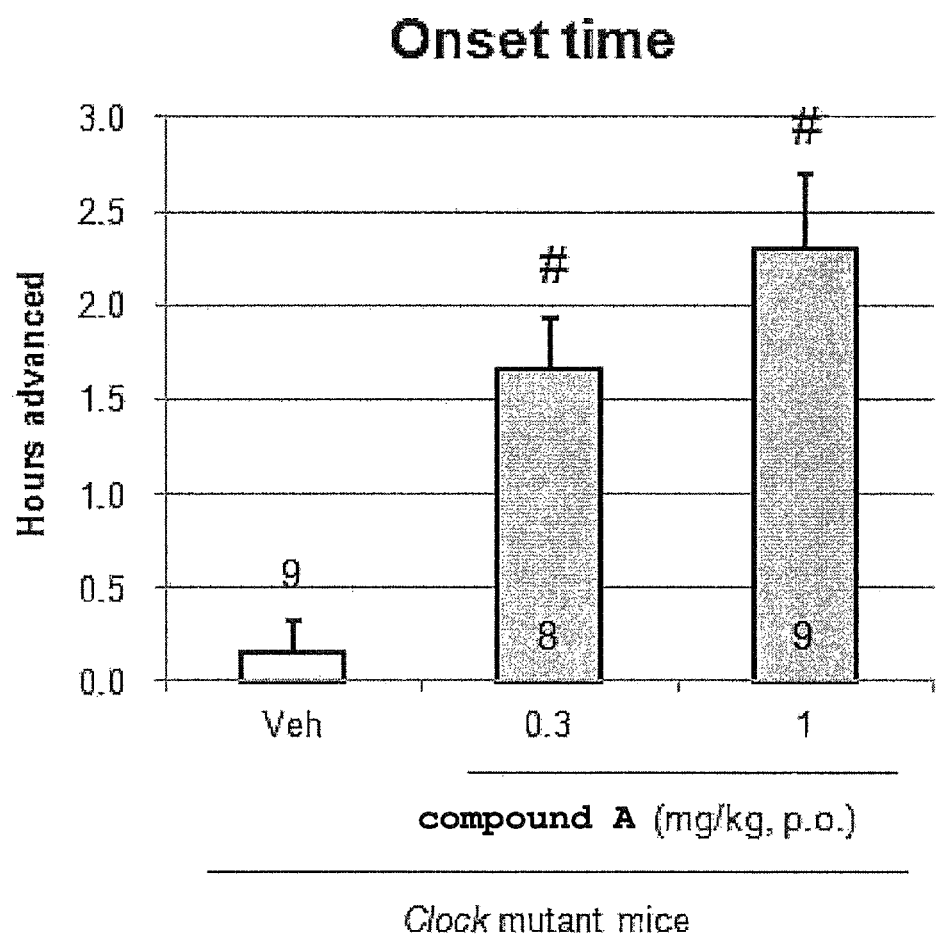
FIG. 2 shows the effect of compound A on the motion start time of Clock mutant mice (Example 1).
Figure 3:
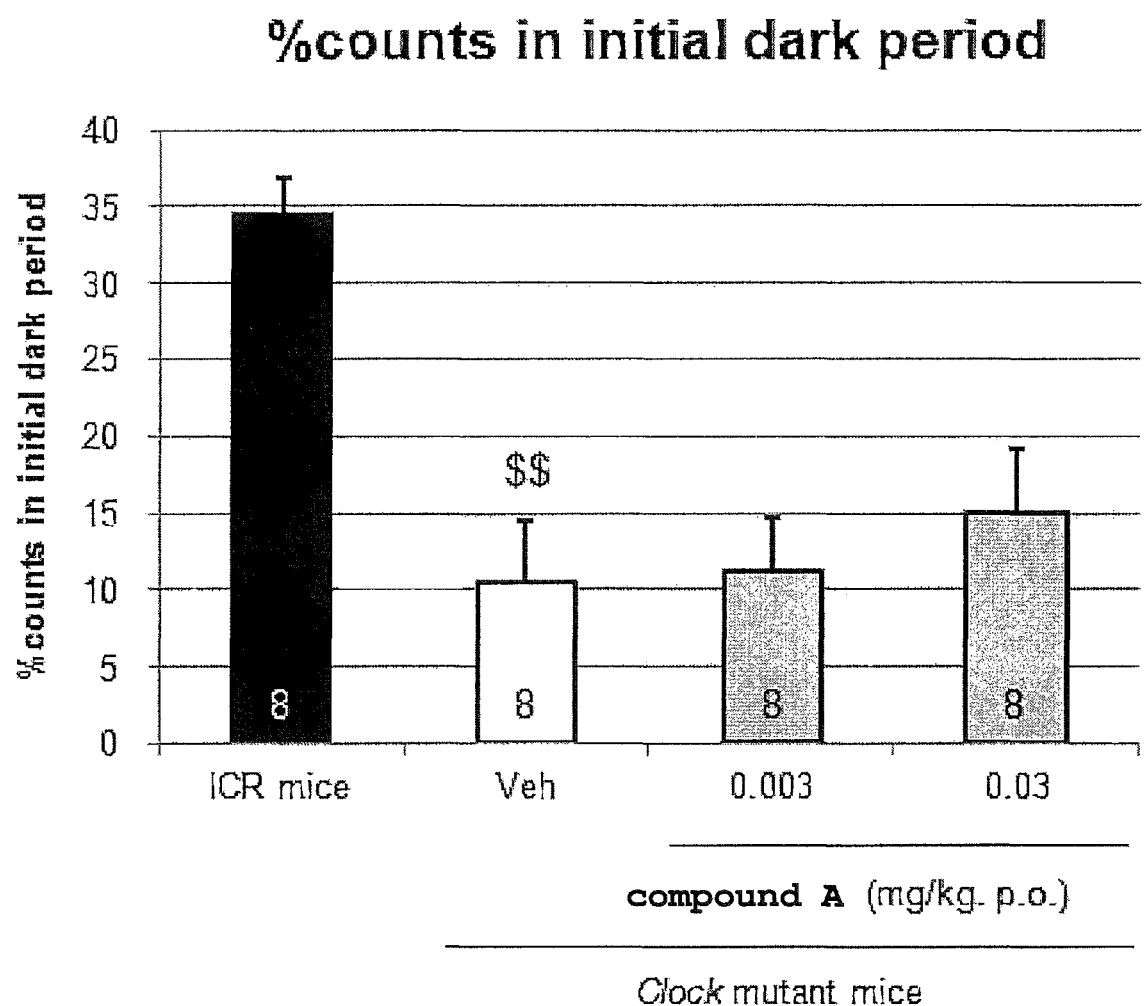
FIG. 3 shows the effect of compound A on Rotating Cage Motion of Clock mutant mice (Example 2).
Figure 4:
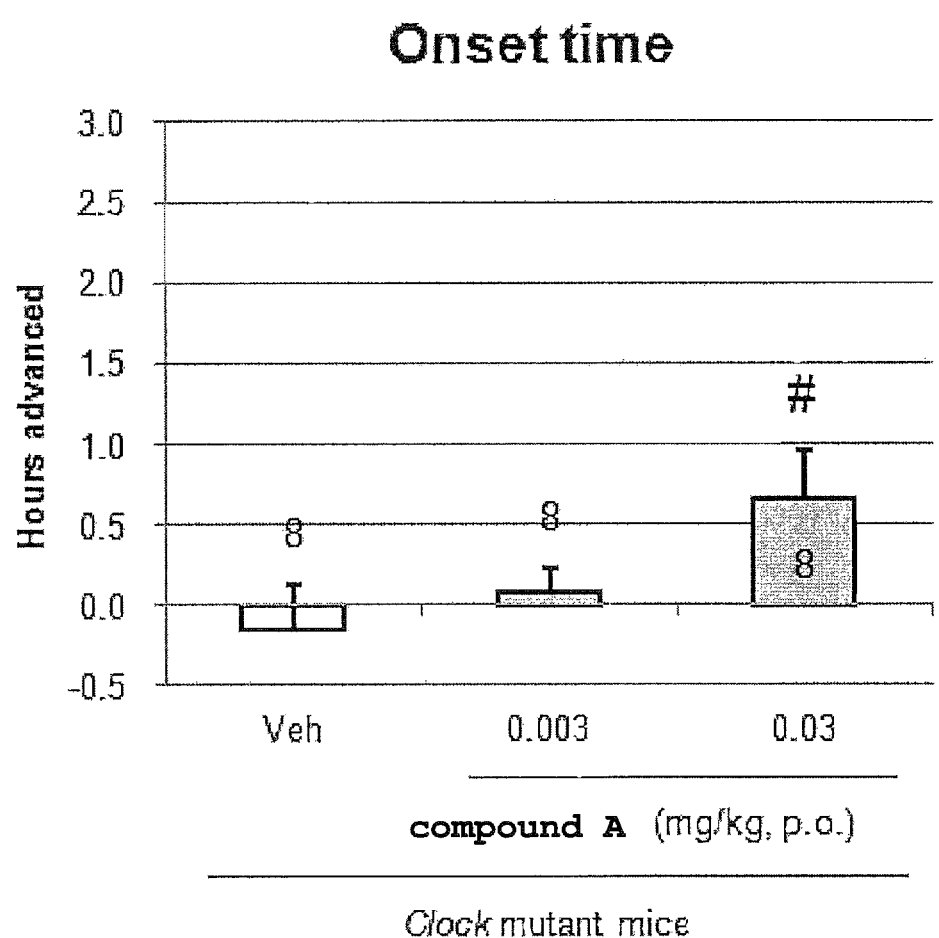
FIG. 4 shows the effect of compound A on the motion start time of Clock mutant mice (Example 2).

The solvent-treated Clock mutant mice showed significantly low % values in the initial dark period than ICR mice (FIGS. 1 and 3), and this characteristically suggests phase retardation in rotating basket exercise of Clock mutant 30 mouse. This decrease was recovered in a dose-dependent manner by the treatment with compound A, and the improvement effect was significant at the both doses of 0.3 and 1 mg/kg (FIG. 1). Compound A at low doses (0.003 and 0.03 mg/kg) did not have a significant effect on the parameter thereof (FIG. 3). Repetitive administration of compound A at a doses of 0.03 (FIG. 4), 0.3 and 1 mg/kg (FIG. 2) significantly advanced the exercise starting time in Clock mutant mouse as compared to an average of the 7-day preliminary treatment period (days 8-14).

These results show that compound A at the minimum effective dose of 0.03 mg/kg progressed phase retardation in Clock mutant mouse and suggest that compound A improves delirium.

Example 2

Effect of Compound A on Nocturnal Plasma Melatonin Concentration in Rats

1. Method
1.1 Animal

9-Week-old male Wistar rats (CLEA Japan Inc.) were used for this study. All rats (n=12) were bred in groups of 2 to 5 animals per cage in a light control room (lights on at 7:00 and 12 hour light/dark cycle) prior to the test and made to get used to it for about two weeks. Food and tap water were freely provided.

1.2 Measurement

A solvent or compound A was orally administered to 11-week-old rats at a dose of 3 mg/kg once per day at 17:00-17:15 for 7 days. After the final treatment, blood samples (500 µL) were successively collected from the tail artery of each rat at 20:00 (ZT (Zeitgeber Time)) 13), 22:00 (ZT15), 0:00 (ZT17), 2:00 (ZT19), 4:00 (ZT21), 6:00 (ZT23) and 8:00 (ZT25) in EDTA-2Na-containing tube (Lot No. MP0831, CAPIJECT (registered trade mark), Terumo Corporation, Japan). The blood samples were centrifuged at 15,000 rpm, 4° C. for 5 min and the supernatant (200 µL) was preserved at -80° C. until they were treated for radioimmunoassay. Melatonin concentration was measured using a kit (Lot No. 2428.10, BUHLMANN Laboratories AG, Switzerland) commercially available from T.N. TECHNOS., Limited, Japan.

1.3 Statistics

The data are shown in average ±SEM (6 rats in each group). The statistical significance between samples and in samples was determined by repeated measurement ANOVA in which P<0.05 was significant.

2. Results and Discussion

Figure 5:
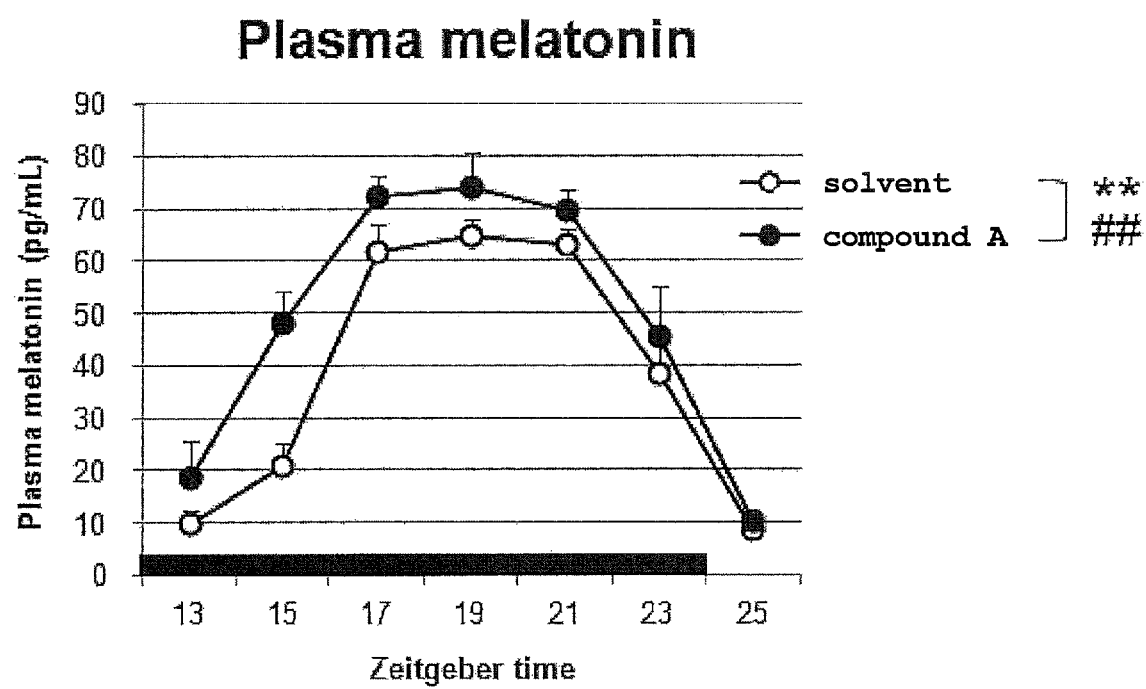
FIG. 5 shows the effect of compound A on the nocturnal plasma melatonin concentration in rats.

Repetitive treatment with compound A at a dose of 3 mg/kg for 7 days advanced the start of plasma melatonin and significantly increased the level of melatonin concentration as compared to a vehicle treatment control (FIG. 5). The time in the Figure shows Zeitgeber Time in which the start time of light cycle is ZT0 and the start time of dark cycle is ZT12.

These results show that compound A induced an increase in endogenous plasma melatonin in rats and suggest that compound A improves delirium.

Preparation Example 1

Compound A (160 g), lactose (4064 g), and cornstarch (640 g) were uniformly mixed in a fluid bed dryer granulator, and the mixture was granulated while spraying an aqueous solution of hydroxypropylcellulose (160 g) therein and dried therein. The obtained granulated product was crushed using a power mill with a 1.5 mmφ punching screen to give a sieved powder. The sieved powder (3894 g) was measured, cornstarch (124 g) and magnesium stearate (12.4 g) were added thereto, and they were mixed to give granules for tabletting. The granules were tableted by a tableting machine with a 7.0 mmφ pounder to a weight of 130 mg to give uncoated tablets. A solution of titanium oxide, yellow ferric oxide dispersed in hydroxypropylmethylcellulose 2910, copolyvidone was sprayed on the obtained uncoated tablets in the film coating machine to give about 25000 film-coated tablets containing 4 mg of compound A per tablet and having the formulation shown in Table 1.

TABLE 1

| composition | amount (mg) |
| --- | --- |
| compound A | 4.0 |
| lactose | 101.6 |
| cornstarch | 20.0 |
| hydroxypropylcellulose | 4.0 |
| magnesium stearate | 0.4 |
| uncoated tablet | 130.0 |
| hydroxypropylmethylcellulose 2910 | 3.74 |

TABLE 1-continued

| composition | amount (mg) |
|---|---|
| copolyvidone | 0.75 |
| titanium oxide | 0.5 |
| yellow ferric oxide | 0.01 |
| total | 135.0 |

INDUSTRIAL APPLICABILITY

According to the present invention, a pharmaceutical agent containing a compound possibly having melatonin receptor affinity as an active ingredient and expected to be effective for the prophylaxis or treatment of delirium can be provided.

This application is based on a U.S. provisional patent application No. 62/276,366, the contents of which are incorporated in full herein.

The invention claimed is:

1. A method for preventing or treating delirium comprising administering an effective amount of (S)—N-[2-(2-methyl-7,8-dihydro-6H-indeno[5,4-d][1,3]oxazol-8-yl)ethyl]acetamide or a salt thereof to a mammal in need thereof.

* * * * *